(12) United States Patent
Oda

(10) Patent No.: US 8,433,390 B2
(45) Date of Patent: Apr. 30, 2013

(54) MAGNETIC RESONANCE IMAGING APPARATUS AND METHOD

(75) Inventor: Yoshihiro Oda, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 222 days.

(21) Appl. No.: 13/016,560

(22) Filed: Jan. 28, 2011

(65) Prior Publication Data

US 2011/0190620 A1    Aug. 4, 2011

(30) Foreign Application Priority Data

Jan. 29, 2010   (JP) .................................. 2010-019312

(51) Int. Cl.
*A61B 5/05*    (2006.01)
(52) U.S. Cl.
USPC ............ 600/410; 324/307; 324/309; 600/407
(58) Field of Classification Search .................... None
See application file for complete search history.

(56) References Cited

U.S. PATENT DOCUMENTS

| | | | |
|---|---|---|---|
| 6,377,044 B1 | 4/2002 | Burl et al. | |
| 6,500,122 B1 | 12/2002 | Washburn et al. | |
| 6,724,923 B2 | 4/2004 | Ma et al. | |
| 7,259,559 B2 | 8/2007 | Nabetani et al. | |
| 7,639,008 B2 | 12/2009 | Ookawa | |
| 2005/0275402 A1* | 12/2005 | Campagna | 324/309 |

FOREIGN PATENT DOCUMENTS

JP    2006-175058    7/2006

* cited by examiner

*Primary Examiner* — Unsu Jung
*Assistant Examiner* — Rajeev Siripurapu
(74) *Attorney, Agent, or Firm* — Armstrong Teasdale LLP

(57) ABSTRACT

A magnetic resonance imaging apparatus scans a region including a predetermined part of a subject to acquire magnetic resonance signals. The magnetic resonance imaging apparatus includes a plurality of coil elements, a calculation device for calculating a proportion of the predetermined part to a first scan region of a first subject and a position of the predetermined part, based on magnetic resonance signals acquired from the first scan region, a prediction device for predicting a region of the predetermined part from within a second scan region of a second subject, based on the proportion and position of the predetermined part related to the first subject, the proportion and position being calculated by the calculation device, and a coil element selection device for selecting at least one coil element used to receive each magnetic resonance signal in the second scan region from within the coil elements, based on the region of the predetermined part predicted by the prediction device.

20 Claims, 27 Drawing Sheets

FIG. 9

|  | OVERLAP REGION | VOLUME Vover |
|---|---|---|
| PREDICTED REGION RH AND SENSITIVE REGION CR1 | VR1 | v1 |
| PREDICTED REGION RH AND SENSITIVE REGION CR2 | VR2 | v2 |
| PREDICTED REGION RH AND SENSITIVE REGION CR3 | VR3 | v3 |

FIG. 10

|  | VOLUME RATE Cp(%) | VOLUME RATE Csense(%) |
|---|---|---|
| PREDICTED REGION RH AND SENSITIVE REGION CR1 | 15(%) | 10(%) |
| PREDICTED REGION RH AND SENSITIVE REGION CR2 | 80(%) | 80(%) |
| PREDICTED REGION RH AND SENSITIVE REGION CR3 | 100(%) | 50(%) |

| | PROPORTION P | POSITION G | PROTOCOL |
|---|---|---|---|
| FIRST SUBJECT | 25(%) | G1 | Px |

FIG. 16

| | OVERLAP REGION | VOLUME Vover |
|---|---|---|
| PREDICTED REGION RH AND SENSITIVE REGION CR1 | — | ZERO |
| PREDICTED REGION RH AND SENSITIVE REGION CR2 | VR2 | v21 |
| PREDICTED REGION RH AND SENSITIVE REGION CR3 | VR3 | v31 |

FIG. 17

| | VOLUME RATE Cp(%) | VOLUME RATE Csense(%) |
|---|---|---|
| PREDICTED REGION RH AND SENSITIVE REGION CR1 | 0(%) | 0(%) |
| PREDICTED REGION RH AND SENSITIVE REGION CR2 | 100(%) | 30(%) |
| PREDICTED REGION RH AND SENSITIVE REGION CR3 | 100(%) | 15(%) |

FIG. 18

| | PROPORTION P | POSITION G | PROTOCOL |
|---|---|---|---|
| FIRST SUBJECT | 25(%) | G1 | Px |
| SECOND SUBJECT | 26(%) | G2 | Px |

| | VOLUME RATE Cp(%) | VOLUME RATE Csense(%) |
|---|---|---|
| PREDICTED REGION RH AND SENSITIVE REGION CR1 | 50(%) | 8(%) |
| PREDICTED REGION RH AND SENSITIVE REGION CR2 | 50(%) | 100(%) |
| PREDICTED REGION RH AND SENSITIVE REGION CR3 | 100(%) | 100(%) |

|  | PROPORTION P | POSITION G | PROTOCOL |
|---|---|---|---|
| FIRST SUBJECT | 25(%) | G1 | Px |
| SECOND SUBJECT | 26(%) | G2 | Px |
| THIRD SUBJECT | 28(%) | G3 | Px |

|  | PROPORTION P | POSITION G | PROTOCOL |
|---|---|---|---|
| FIRST SUBJECT | 25(%) | G1 | Px |
| SECOND SUBJECT | 26(%) | G2 | Px |
| THIRD SUBJECT | 28(%) | G3 | Px |
| ⋮ | ⋮ | ⋮ | ⋮ |
| n-2TH SUBJECT | 25(%) | Gn-2 | Px |
| n-1TH SUBJECT | 30(%) | Gn-1 | Px |

FIG. 26

|  | PROPORTION P | POSITION G | PROTOCOL |
|---|---|---|---|
| FIRST SUBJECT | 25(%) | G1 | Px |
| SECOND SUBJECT | 26(%) | G2 | Px |
| THIRD SUBJECT | 28(%) | G3 | Px |
| ⋮ | ⋮ | ⋮ | ⋮ |
| n-2TH SUBJECT | 25(%) | Gn-2 | Px |
| n-1TH SUBJECT | 30(%) | Gn-1 | Px |
| nTH SUBJECT | 34(%) | Gn | Px |

FIG. 27

|  | PROPORTION P | POSITION G | PROTOCOL | HEIGHT |
|---|---|---|---|---|
| FIRST SUBJECT | 25(%) | G1 | Px | m1 |
| SECOND SUBJECT | 26(%) | G2 | Px | m2 |
| THIRD SUBJECT | 28(%) | G3 | Px | m3 |
| ⋮ | ⋮ | ⋮ | ⋮ | ⋮ |
| n-2TH SUBJECT | 25(%) | Gn-2 | Px | mn-2 |
| n-1TH SUBJECT | 30(%) | Gn-1 | Px | mn-1 |
| nTH SUBJECT | 34(%) | Gn | Px | mn |

| | VOLUME RATE Cp(%) | VOLUME RATE Csense(%) |
|---|---|---|
| PREDICTED REGION RH AND SENSITIVE REGION CR11 | 98(%) | 35(%) |
| PREDICTED REGION RH AND SENSITIVE REGION CR12 | 2(%) | 1(%) |
| PREDICTED REGION RH AND SENSITIVE REGION CR13 | 100(%) | 15(%) |

FIG. 35

|  | PROPORTION P | POSITION G | PROTOCOL |
|---|---|---|---|
| FIRST SUBJECT | 25(%) | G1 | Px |
| SECOND SUBJECT | 26(%) | G2 | Px |
| THIRD SUBJECT | 28(%) | G3 | Px |
| ⋮ | ⋮ | ⋮ | ⋮ |
| n-1TH SUBJECT | 30(%) | Gn-1 | Px |
| nTH SUBJECT | 34(%) | Gn | Px |
| n+1TH SUBJECT | 20(%) | Gn+1 | Px |

FIG. 39

|  | VOLUME RATE Cp(%) | VOLUME RATE Csense(%) |
|---|---|---|
| PREDICTED REGION RH AND SENSITIVE REGION CR11 | 100(%) | 15(%) |
| PREDICTED REGION RH AND SENSITIVE REGION CR12 | 0(%) | 0(%) |
| PREDICTED REGION RH AND SENSITIVE REGION CR13 | 100(%) | 7(%) |

MAGNETIC RESONANCE IMAGING APPARATUS AND METHOD

CROSS REFERENCE TO RELATED APPLICATIONS

This application claims the benefit of Japanese Patent Application No. 2010-019312 filed Jan. 29, 2010, which is hereby incorporated by reference in its entirety.

BACKGROUND OF THE INVENTION

The present invention relates to a magnetic resonance imaging apparatus that scans a subject to acquire magnetic resonance signals.

A multichannel coil having a large number of coil elements has recently been in widespread use as a receiving coil for receiving magnetic resonance signals of a subject. There has been proposed a method for allowing an operator to select coil elements used to receive magnetic resonance signals out of a large number of coil elements according to a scan region of a subject where the subject is imaged using a multichannel coil (refer to Japanese Unexamined Patent Publication No. 2006-175058).

In the above-described method, the operator needs to select the coil elements manually. There has therefore been proposed a method for automatically selecting each coil element according to a scan region set by the operator. Since, however, the operator tends to set the scan region wider than a region of interest, a sensitive region of the selected coil element can become much wider than the region of interest, so that image quality may be deteriorated. It is desirable that the deterioration in image quality is suppressed as much as possible.

BRIEF DESCRIPTION OF THE INVENTION

One aspect of the invention is a magnetic resonance imaging apparatus that scans a region including a predetermined part of a subject to acquire magnetic resonance signals, including: a plurality of coil elements; a calculation device for calculating a proportion of the predetermined part to a first scan region of a first subject and a position of the predetermined part, based on magnetic resonance signals acquired from the first scan region; a prediction device for predicting a region of the predetermined part from within a second scan region of a second subject, based on the proportion and position of the predetermined part related to the first subject, the proportion and position being calculated by the calculation device; and a coil element selection device for selecting at least one coil element used to receive each magnetic resonance signal in the second scan region from within the coil elements, based on the region of the predetermined part predicted by the prediction device.

A region of a predetermined part can be predicted from within a second scan region of a second subject, based on a proportion of the predetermined part and a position thereof related to a first subject. The invention is thus possible to select at least one coil element suitable for imaging of the predetermined part.

Further objects and advantages of the present invention will be apparent from the following description of the preferred embodiments of the invention as illustrated in the accompanying drawings.

BRIEF DESCRIPTION OF THE DRAWINGS

FIG. 9 is a table showing volumes Vover of the overlap regions VR1 through VR3.

FIG. 10 is a diagram illustrating one example illustrative of the values of a volume rate Cp and a volume rate Csense.

FIG. 16 is a table illustrating volumes Vover of the overlap regions VR2 and VR3.

FIG. 17 is a diagram depicting one example illustrative of the values of a volume rate Cp and a volume rate Csense.

FIG. 18 is a conceptual diagram showing the contents stored in the database 10.

FIG. 26 is a schematic diagram showing the contents stored in the database 10.

FIG. 27 is a conceptual diagram illustrating data stored in the database 10 in a second embodiment.

FIG. 35 is a conceptual diagram illustrating the contents stored in the database 10.

FIG. 39 is a diagram showing one example illustrative of the values of a volume rate Cp and a volume rate Csense.

DETAILED DESCRIPTION OF THE INVENTION

Modes for carrying out the invention will be explained hereinafter, but the invention is not limited to the following embodiments.

(1) First Embodiment

Figure 1:
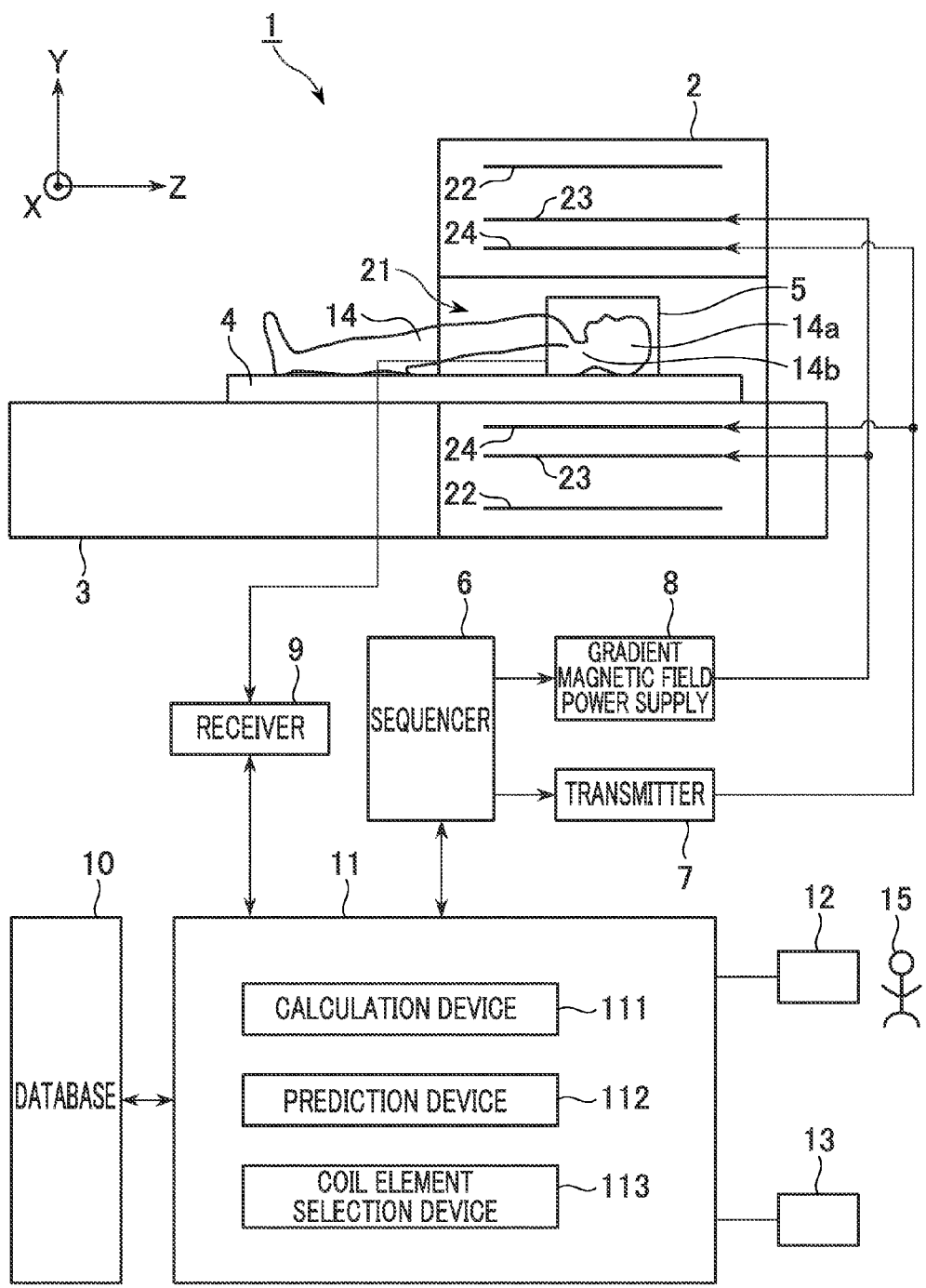
FIG. 1 is a schematic diagram showing a magnetic resonance imaging apparatus 1 according to a first embodiment of the invention.

FIG. 1 is a schematic diagram of a magnetic resonance imaging apparatus 1 according to a first embodiment of the invention.

The magnetic resonance imaging (MRI (Magnetic Resonance Imaging)) apparatus 1 has a magnetic field generator 2, a table 3, a cradle 4, a receiving coil 5, etc.

The magnetic field generator 2 has a bore 21 in which a subject 14 is held, a superconductive coil 22, a gradient coil 23 and a transmitting coil 24. The superconductive coil 22 applies a static magnetic field B0, and the gradient coil 23 applies a gradient magnetic field in a frequency encoding direction, a phase encoding direction and a slice selection direction. The transmitting coil 24 transmits an RF pulse. Incidentally, a permanent magnet may be used instead of the superconductive coil 22.

The cradle 4 is configured so as to be movable from the table 3 to the bore 21. The subject 14 is conveyed to the bore 21 by the cradle 4.

The receiving coil 5 has a plurality of coil elements for receiving magnetic resonance signals. The structure of the receiving coil 5 will be described later.

The MRI apparatus 1 further has a sequencer 6, a transmitter 7, a gradient magnetic field power supply 8, a receiver 9, a database 10, a central processing unit 11, an input device 12 and a display device 13.

Under the control of the central processing unit 11, the sequencer 6 transmits information (center frequency, bandwidth and the like) about an RF pulse to the transmitter 7 and transmits information (strength of gradient magnetic field, etc.) about a gradient magnetic field to the gradient magnetic field power supply 8.

The transmitter 7 outputs a drive signal for driving the transmitting coil 24, based on the information transmitted from the sequencer 6.

The gradient magnetic field power supply 8 outputs a drive signal for driving the gradient coil 23, based on the information transmitted from the sequencer 6.

The receiver 9 signal-processes each magnetic resonance signal received by the receiving coil 5 and transmits it to the central processing unit 11.

The database 10 stores therein information about sensitive regions CR1 through CR3 (refer to FIG. 3, for example) to be described later, and rates P and positions G (refer to FIG. 26, for example) to be described later.

The central processing unit 11 generally controls the operations of respective parts of the MRI apparatus 1 so as to realize various operations of the MRI apparatus 1 such as reconstruction of an image based on each signal received from the receiver 9. The central processing unit 11 has calculation device 111, prediction device 112 and coil element selection device 113, etc.

The calculation device 111 calculates a rate of a predetermined region or part to a scan region and a position thereof, based on magnetic resonance signals acquired from the scan region.

The prediction device 112 predicts a region of the predetermined part from within the scan region, based on the rates P and positions G stored in the database 10.

The coil element selection device 113 selects at least one coil element used to receive each magnetic resonance signal in the scan region out of a plurality of coil elements, based on the region of the predetermined part predicted by the prediction device 112.

The central processing unit 11 is comprised of, for example, a computer. Incidentally, the central processing unit 11 functions as the calculation device 111, prediction device 112 and coil element selection device 113 by executing a predetermined program.

The input device 12 inputs various instructions to the central processing unit 11 in response to the manipulation of an operator 15. The display device 13 displays various information thereon.

The MRI apparatus 1 is configured as described above.

The receiving coil 5 will next be explained concretely.

Figure 2:
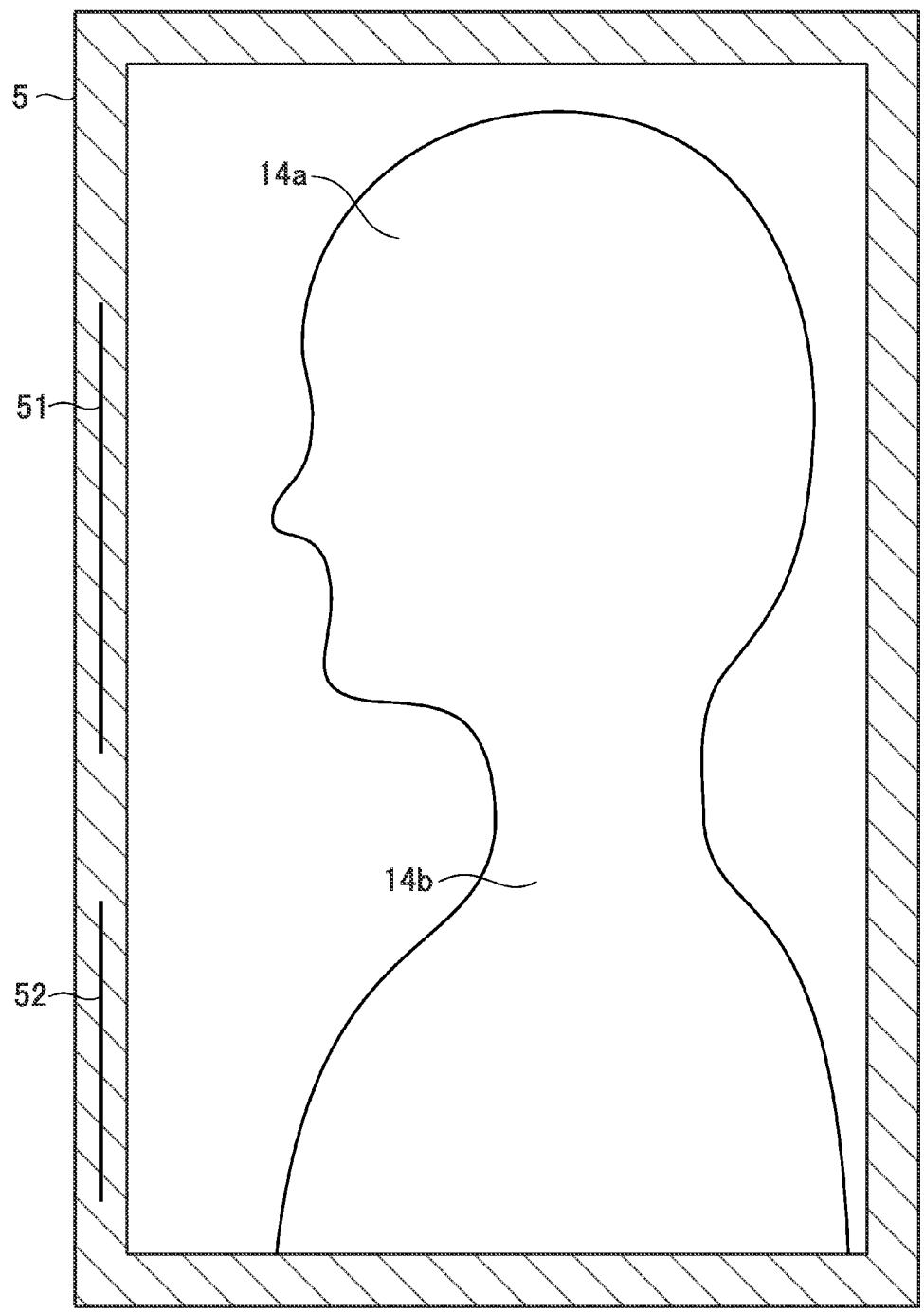
FIG. 2 is a diagram for explaining a receiving coil 5.

FIG. 2 is a diagram for describing the receiving coil 5.

Incidentally, the plane of a subject shown in FIG. 2 is a sagittal plane.

The receiving coil 5 has a plurality of coil elements. Only two coil elements 51 and 52 are shown in FIG. 2 as the coil elements included in the receiving coil 5. Actually, however, the receiving coil 5 has more coil elements. For convenience of explanation, however, the receiving coil 5 will be described below assuming that it has only two coil elements 51 and 52.

When each magnetic resonance signal is received from the subject 14, combinations of coil elements suitable for receiving the magnetic resonance signals of the subject 14 are selected from within the two coil elements 51 and 52. In the first embodiment, three combinations Set1, Set2 and Set3 of coil elements are selectable. The combinations Set1, Set2 and Set3 thereof are as follows:

Set1=coil element 51
Set2=coil element 52
Set3=coil element 51+coil element 52

Namely, the combination Set1 is comprised of the coil element 51, and the combination Set2 is comprised of the coil element 52. Further, the combination Set3 is comprised of the coil elements 51 and 52.

Sensitive regions of the combinations Set1 through Set3 of the coil elements will next be explained.

Figure 3A:
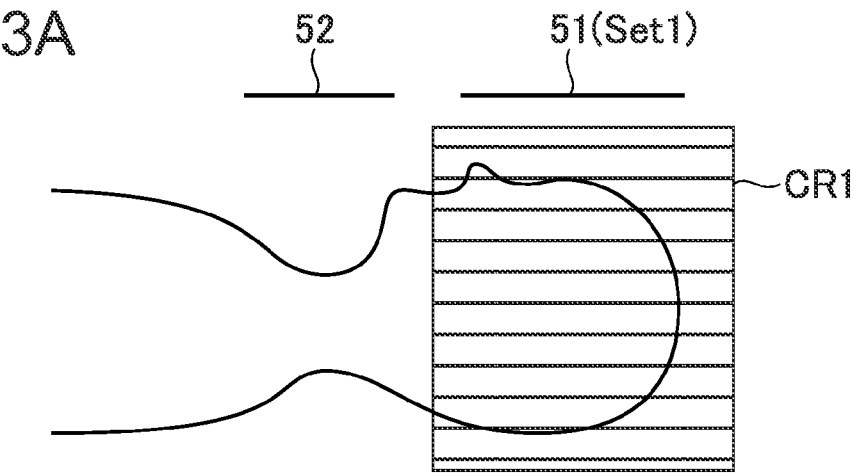
FIGS. 3A, 3B, and 3C are diagrams for explaining sensitive regions of combinations Set1 through Set3 of coil elements.
Figure 3B:
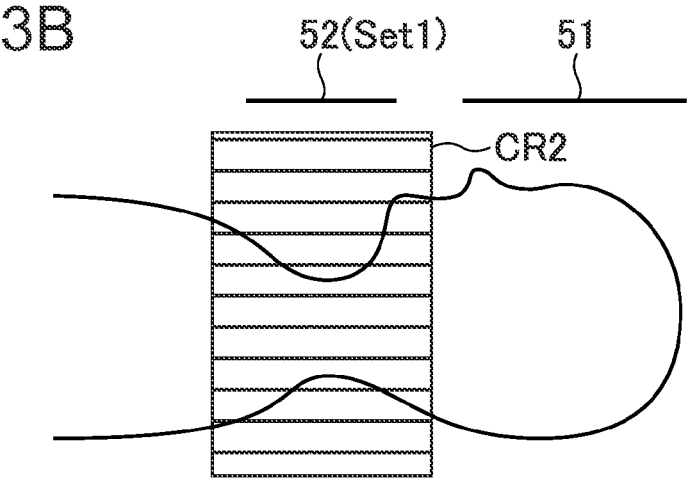
Figure 3C:
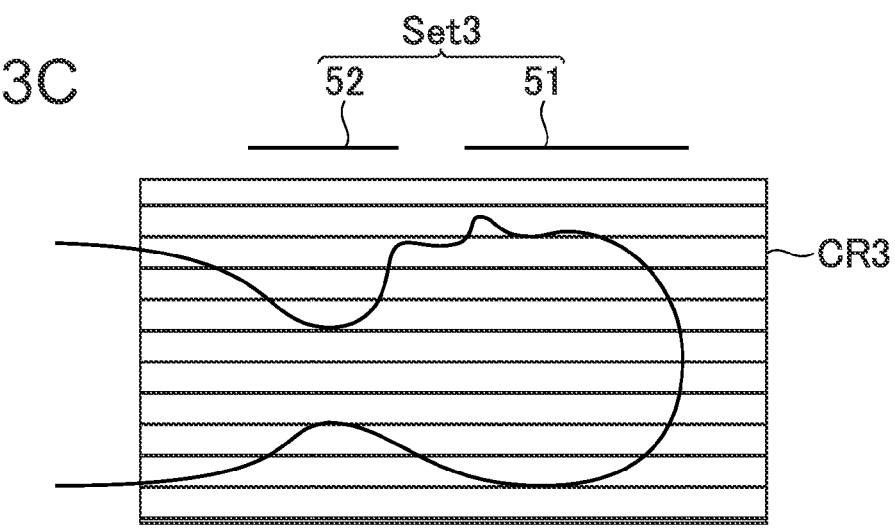

FIGS. 3A, 3B, and 3C are diagrams for describing the sensitive regions of the combinations Set1 through Set3.

FIGS. 3A through 3C respectively show the sensitive regions CR1 through CR3 (hatched portions) of the combinations Set1 through Set3. For example, the sensitive region CR1 (refer to FIG. 3A) is a region in which the combination Set1 is considered to have sensitivity enough to obtain a high-quality MR image. The extent of the sensitive region CR1 is determined based on a sensitivity characteristic of the combination Set1, which has been examined in advance.

Information (position information about the sensitive region CR1, the volume of the sensitive region CR1, etc.) about the sensitive region CR1 has been stored in the database 10. Incidentally, the sensitive region CR1 may be defined as one region such as a cone, a cylinder, a sphere, a polyhedron, a columnar body, a rectangular parallelepiped, a cube or the like. Alternatively, it may be defined as a combination of plural regions.

Although the above description has been made of the sensitive region CR1 of the combination Set1, the sensitive regions CR2 and CR3 of other combinations Set2 and Set3 are also similar to the above.

The sensitive regions CR1 through CR3 of the combinations Set1 through Set3 are defined as described above.

A processing flow of the MRI apparatus 1 will next be described. Incidentally, the following description will be made of a processing flow taken where n subjects are imaged or scanned in order.

Figure 4:
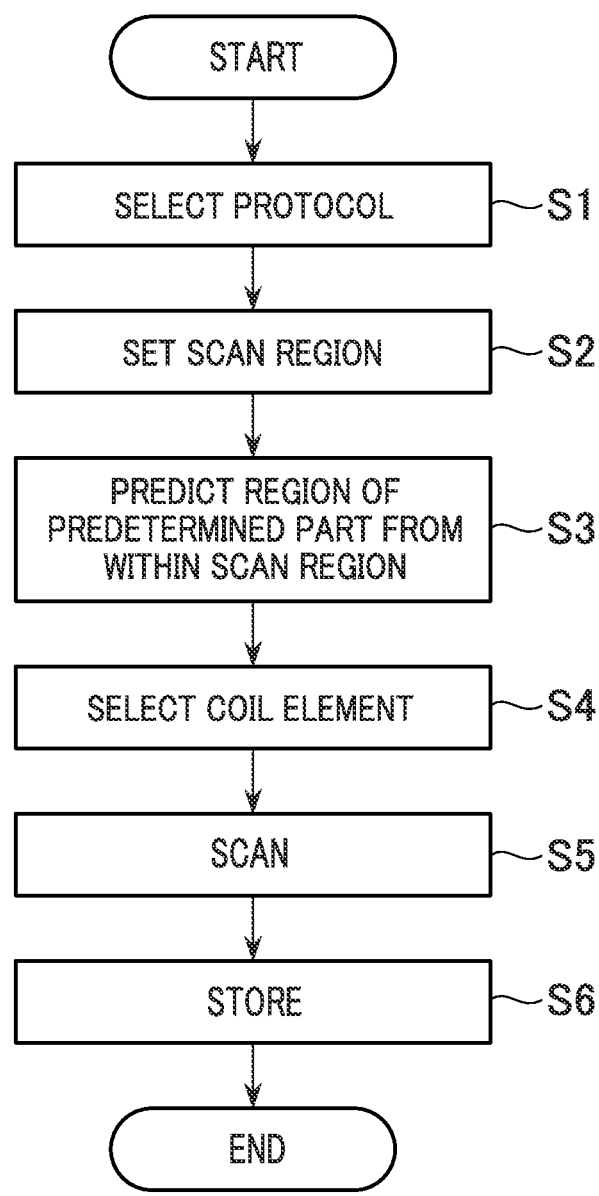
FIG. 4 is a diagram showing one example of a processing flow of the MRI apparatus 1.

FIG. 4 is a diagram showing one example of the processing flow of the MRI apparatus 1.

At Step S1, the operator 15 places a first subject 14 on the cradle and installs the receiving coil 5 thereon. The operator 15 selects a protocol used when the first subject 14 is imaged, according to an imaging region of the first subject 14 and imaging purposes. Here, the protocol is of a protocol that defines the type of scan or the like executed to image the subject 14. In the protocol, a plurality of types are prepared according to the imaging region and purpose. The operator 15 selects a predetermined protocol from within a plurality of types of protocol P1 through Pn according to the imaging region and purpose. Here, assume that a protocol Px suitable for the imaging of the neck 14b of the subject 14 has been selected. Scans executed to acquire image data used when setting each scan region, imaging scans (such as a T1 scan, a T2 scan and a Flair scan) executed to acquire image data necessary to perform a medial diagnosis of the neck 14b, etc. have been defined in the selected protocol Px. After the protocol Px has been selected, the processing flow proceeds to Step S2.

At Step S2, a scan for acquiring image data used upon the setting of the scan region is performed. The scan region is set referring to an MR image obtained by this scan (refer to FIG. 5).

Figure 5:
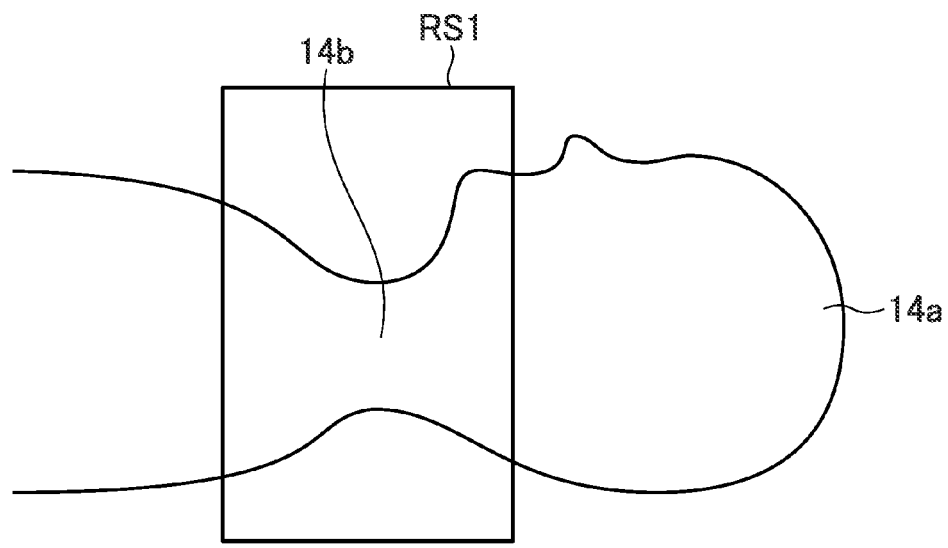
FIG. 5 is a diagram illustrating a set scan region.

FIG. 5 is a diagram showing the set scan region.

At Step S2, the operator 15 sets a slice position and a slice thickness or the like to thereby set a scan region RS1 taken when the neck 14b of the first subject 14 is scanned. After the scan region RS1 has been set, the processing flow proceeds to Step S3.

Figure 6:
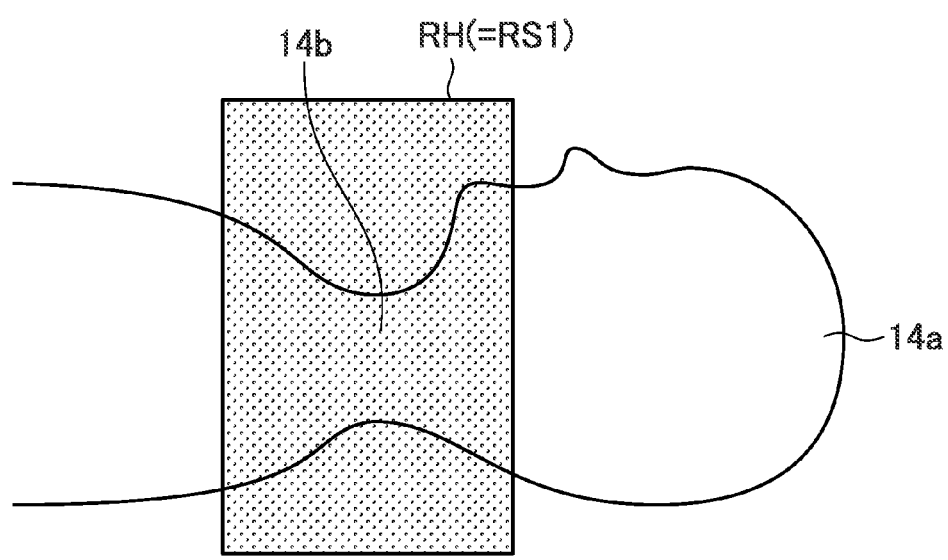
FIG. 6 is a diagram depicting a predicted region RH of neck 14b.

At Step S3, the prediction device 112 (refer to FIG. 1) predicts a region for the neck 14b from within the scan region RS1, based on the rates P and positions G (refer to FIG. 26 to be described later, for example) stored in the database 10. Incidentally, assume here that the rates and positions are not yet stored in the database 10. In this case, the prediction device 112 predicts 100% (i.e., the whole of the scan region RS1) of the scan region RS1 as a region RH for the neck 14b. In FIG. 6, the predicted region RH of neck 14b is expressed in a large number of dots. It is understood that referring to FIG. 6, the scan region RS1 matches or coincides with the predicted region RH of neck 14b. After the region RH of the neck 14b has been predicted, the processing flow proceeds to Step 4.

At Step S4, the coil element selection device 113 (refer to FIG. 1) selects the corresponding combination of coil elements used to receive each magnetic resonance signal from within the three combinations Set1 through Set3 (refer to FIG. 3), based on the region RH of the neck 14b predicted at Step S3. A description will be made below of how the combination thereof is selected at Step S4.

Figure 7:
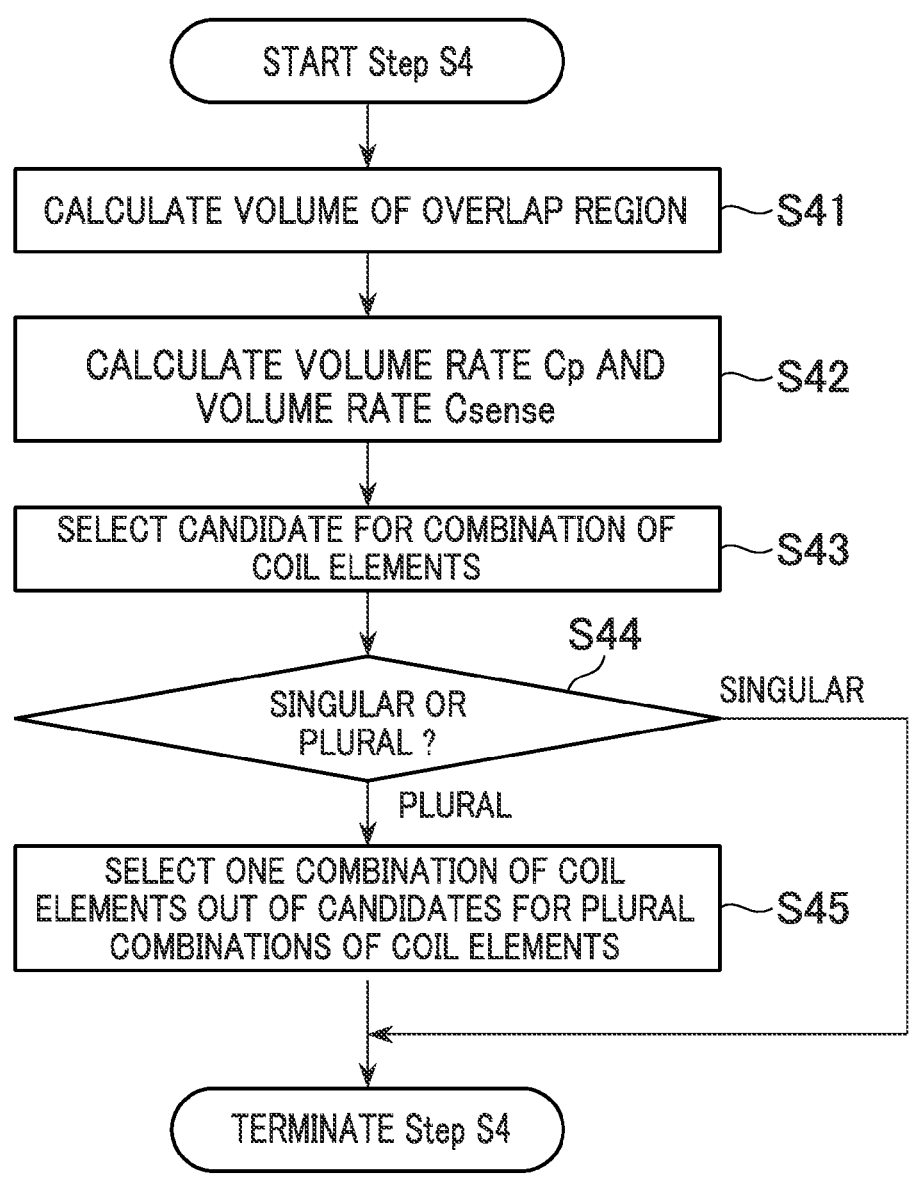
FIG. 7 is a diagram showing one example of a flow of Step S4.

FIG. 7 is a diagram showing one example of a flow of Step S4.

At Substep S41, the coil element selection device 113 first calculates the volumes of portions (hereinafter called "overlap regions") that overlap between the sensitive regions CR1 through CR3 of the combinations Set1 through Set3 of the coil elements and the predicted region RH (scan region RS1) of neck 14b (refer to FIGS. 8 and 9).

Figure 8A:
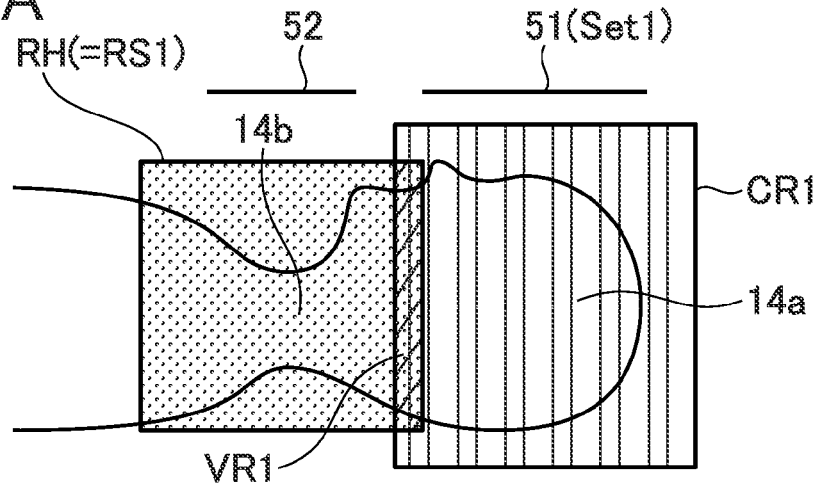
FIGS. 8A, 8B, and 8C are diagrams illustrating overlap regions VR1 through VR3 between the sensitive regions CR1 through CR3 of the combinations Set1 through Set3 of the coil elements and the predicted region RH.
Figure 8B:
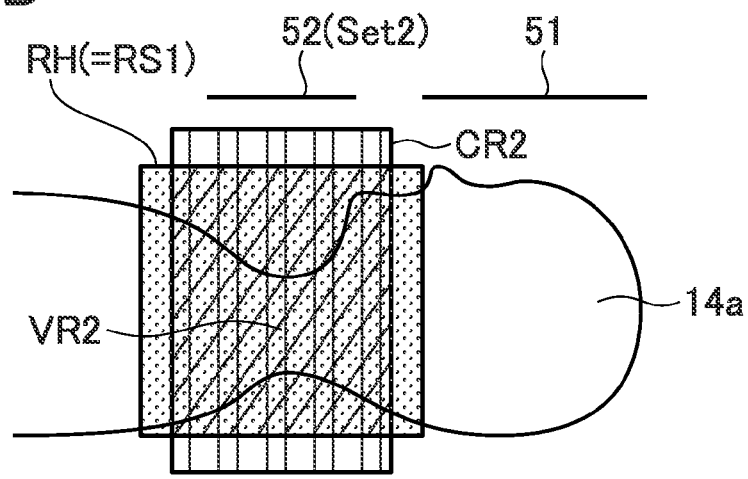
Figure 8C:
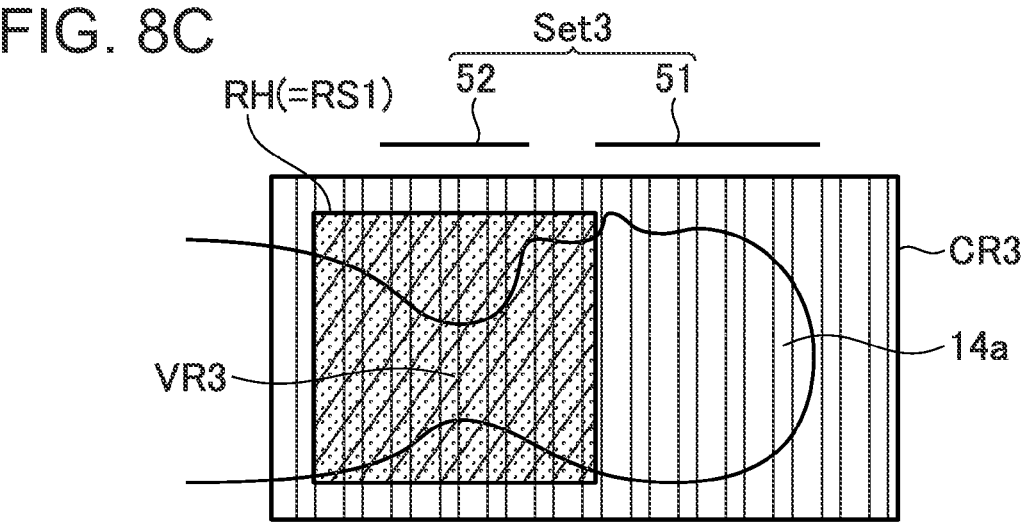

FIGS. 8A, 8B, and 8C are diagrams showing the overlap regions VR1 through VR3 between the sensitive regions CR1 through CR3 of the combinations Set1 through Set3 and the predicted region RH. The overlap regions VR1 through VR3 are represented in diagonal lines in FIGS. 8A, 8B, and 8C.

FIG. 9 is a table showing the volumes Vover of the overlap regions VR1 through VR3. For convenience of explanation, the volumes Vover of the overlap regions VR1 through VR3 are represented in the form of characters of v1 through v3 in FIG. 9.

After the volumes of the overlap regions have been determined, the flow proceeds to Substep S42.

At Substep S42, the coil element selection device 113 calculates two volume rates Cp and Csense, based on the volumes Vover of the overlap regions VR1 through VR3 calculated at Substep S41. The two volume rates Cp and Csense will be explained below in order.

(1) Concerning the Volume Rate Cp:

The volume rate Cp is of an index indicative of a proportion of the overlap region to the predicted region RH of neck 14b. In the first embodiment, the volume rate Cp is expressed in the following equation:

$$Cp=(Vover/Vp) \times 100(\%) \quad (1)$$

where Vover: respective volumes of overlap regions VR1 through VR3, and Vp: volume of predicted region RH of neck 14b Accordingly, it means that as the volume rate Cp increases, the proportion of overlap of the predicted region RH of neck 14b on each sensitive region is larger. On the other hand, it means that as the volume rate Cp decreases, the proportion of overlap of the predicted region RH of neck 14b on each sensitive region is smaller. Vover of the equation (1) has been calculated at Substep S41. Vp can also be calculated based on the predicted region RH of neck 14b. Accordingly, the value of Vover and the value of Vp are substituted into the equation (1) to thereby calculate the volume rate Cp for each of combinations of the predicted region RH of neck 14b and the sensitive regions CR1 through CR3.

(2) Concerning Volume Rate Csense:

The volume rate Csense is of an index indicative of the proportion of the overlap region to its corresponding sensitive region. In the first embodiment, the volume rate Csense is expressed in the following equation:

$$Csense=(Vover/Vsense) \times 100(\%) \quad (2)$$

where Vover: respective volumes of overlap regions VR1 through VR3, and Vsense: respective volumes of sensitive regions CR1 through CR3

Accordingly, it means that as the volume rate Csense increases, the proportion of coincidence (compatibility) of each sensitive region with its corresponding overlap region is larger. It means that as the volume rate Csense decreases, the proportion of coincidence (compatibility) of each sensitive region with its corresponding overlap region is smaller. Vover of the equation (2) has been calculated at Substep S41. Vsense has been stored in the database 10. Accordingly, the value of Vover and the value of Vsense are substituted into the equation (2) to thereby calculate the volume rate Csense for each of combinations of the predicted region RH of neck 14b and the sensitive regions CR1 through CR3.

The volume rate Cp and the volume rate Csense are calculated in the above-described manner. One example illustrative of the values of the volume rate Cp and the volume rate Csense is shown in FIG. 10 for each of the combinations of the predicted region RH of neck 14b and the sensitive regions CR1 through CR3.

After the volume rate Cp and the volume rate Csense have been calculated, the flow proceeds to Substep S43.

At Substep S43, the coil element selection device 113 selects a candidate for the corresponding combination of coil elements used to receive magnetic resonance signals in the scan region RS1, out of the combinations Set1 through Set3 (refer to FIG. 8), based on the value of each volume rate Cp.

As mentioned above, the larger the value of the volume rate Cp, the greater the proportion of overlap of the predicted region RH of neck 14b on each sensitive region. Thus, at Substep S43, the combination of coil elements, having the sensitive region at the time that the volume rate Cp becomes a maximum value, is selected as a candidate for the combination of the coil elements used to receive the magnetic resonance signals in the scan region RS1. Here, the maximum value of the volume rate Cp is 100(%) (refer to FIG. 10). Since the sensitive region at the time that Cp=100(%) corresponds to the sensitive region CR3, the combination Set3 having the sensitive region CR3 is selected as a candidate for the corresponding combination of coil elements at Substep S43. After the combination Set3 has been selected, the flow proceeds to Substep S44.

At Substep S44, the coil element selection device 113 determines whether the candidate for the combination selected at Substep S43 is singular or plural. When only one candidate for the combination is selected, the corresponding candidate is decided as the combination of the coil elements used upon receiving each magnetic resonance signal, and the processing flow is terminated. On the other hand, when the plural candidates are selected, the flow proceeds to Substep S45. Since only one candidate (Set3) for the combination is selected here, the combination Set3 of the coil elements is determined as the combination of the coil elements used when the magnetic resonance signals are received. Thus, the flow shown in FIG. 7 is terminated. After the combination of the coil elements has been determined, the processing flow proceeds to Step S5 (refer to FIG. 4).

At Step S5, an imaging scan is carried out using the combination Set3 selected at Step S4. After the imaging scan has been executed, the processing flow proceeds to Step S6.

At Step S6, the calculation device 111 (refer to FIG. 1) calculates a proportion P of the neck 14b to the scan region RS1 and a position G of the neck 14b, based on the magnetic resonance signals acquired by executing the scan at Step S5. In order to calculate the proportion P of the neck 14b and the position G thereof, the calculation device 111 (refer to FIG. 1) first extracts the neck 14b from within the scan region RS1 (refer to FIG. 11).

Figures 11, 12:
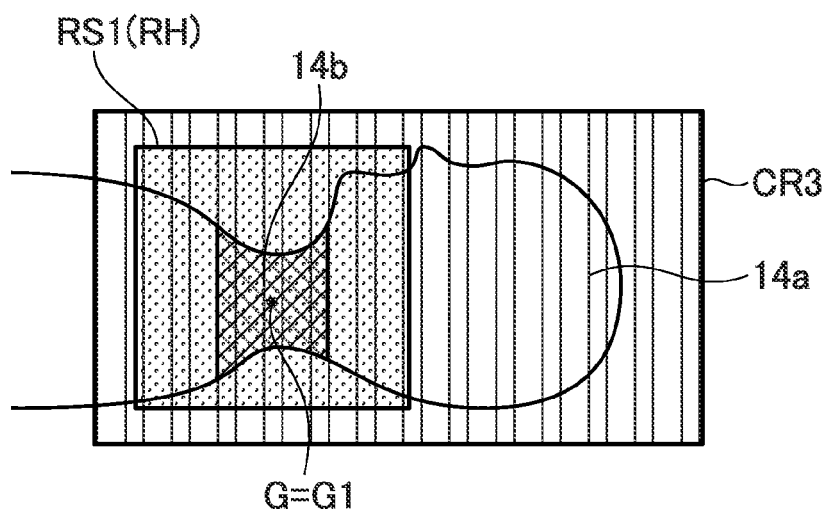
FIG. 11 is a diagram showing a neck 14b extracted from within a scan region RS1.
FIG. 12 is a conceptual diagram showing the contents stored in a database 10.

FIG. 11 is a diagram showing the neck 14b extracted from within the scan region RS1.

Since the cross-section or plane of the neck 14b is narrower than that of the head and that of the shoulder, the corresponding neck 14b can be extracted from within the scan region RS1 by a method such as an analysis of a signal strength distribution of magnetic resonance signals for each slice set at Step S2. The extracted neck 14b is shown cross-hatched in FIG. 11. The neck 14b of the first subject 14 is extracted to thereby calculate a proportion P of the neck 14b to the scan region RS1 and a position G of the neck 14b. In the first embodiment, the position G of the neck 14b is calculated as the position relative to the scan region. Thus, at the first subject 14, the position G of the neck 14b thereof is calculated as the position relative to the scan region RS1. Incidentally, in the first embodiment, the position of center of gravity of the neck 14b is calculated as the position G of the neck 14b, but a position different from the position of center of gravity of the neck 14b may be calculated. Assume here that the proportion P=25% and the position G=G1. The calculated proportion P and position G of neck 14b are stored in the database 10 in relation to the protocol used when the first subject 14 is imaged (refer to FIG. 12).

FIG. 12 is a conceptual diagram showing the contents stored in the database 10.

The proportion P of the neck 14b to the scan region RS1 of the first subject 14 and the position G thereof are stored in the database 10 corresponding to the protocol used when the first subject 14 is imaged. Since the protocol Px is selected at Step S1 where the first subject 14 is imaged, the proportion P and position G of the first subject 14 are stored corresponding to the protocol Px.

The processing flow shown in FIG. 4 is terminated in the above-described manner.

After the first subject 14 has been imaged, a second subject 14 is imaged. The imaging of the second subject 14 will also be explained with reference to the flowcharts shown in FIGS. 4 and 7.

At Step S1, the operator 15 places a second subject 14 on the cradle and installs the receiving coil 5 thereon. The operator 15 selects a protocol used when the second subject 14 is imaged, according to an imaging region of the second subject 14 and imaging purposes. Assume here that the protocol Px suitable for imaging of the neck 14b is selected in a manner similar to when the first subject 14 is imaged. After the protocol Px has been selected, the processing flow proceeds to Step S2.

At Step S2, a scan for acquiring image data used upon setting the scan region is performed. Then the scan region is set referring to an MR image obtained by this scan (refer to FIG. 13).

Figure 13:
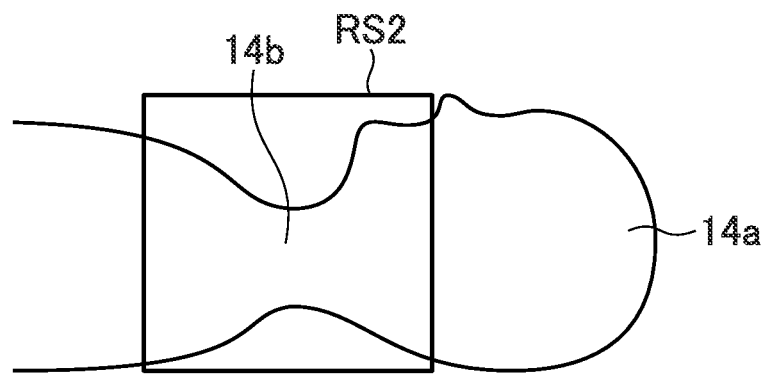
FIG. 13 is a diagram illustrating a set scan region.

FIG. 13 is a diagram showing the set scan region.

At Step S2, the operator 15 sets a slice position and a slice thickness or the like to thereby set a scan region RS2 taken when the neck 14b of the second subject 14 is scanned. After the scan region RS2 has been set, the processing flow proceeds to Step S3.

At Step S3, the prediction device 112 predicts the region for the neck 14b from within the scan region RS2, based on the proportions P and positions G stored in the database 10. In order to predict the region of the neck 14b, the prediction device 112 first determines whether a proportion P and a position G associated with the same protocol as the protocol Px selected when the second subject 14 is imaged, are stored in the database 10. The proportion P and the position G of the neck 14b, which have been stored when the first subject 14 is imaged, are stored in the database 10 in association with the protocol Px (refer to FIG. 12). It is thus understood that the protocol Px selected upon imaging the second subject 14 is identical to the protocol selected upon imaging the first subject 14. In this case, a region RH for the neck 14b is predicted from within the scan region RS2 on the basis of the proportion P (=25%) and position G (=G1) of the neck 14b both stored in the database 10.

Figure 14:
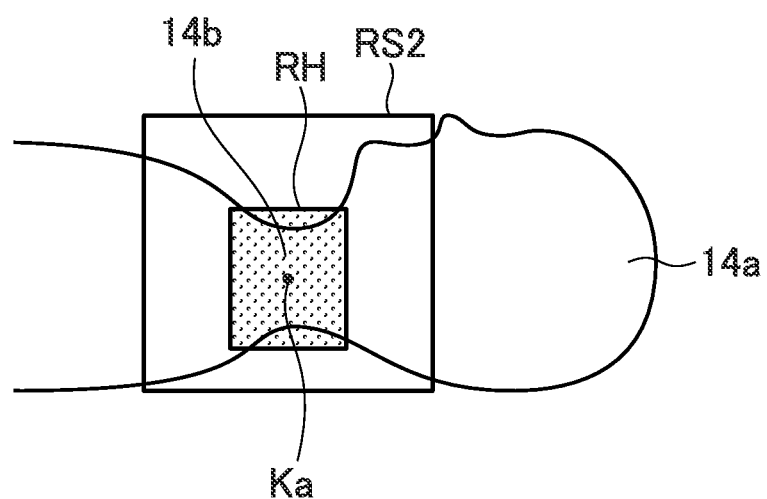
FIG. 14 is a schematic diagram depicting a predicted region of neck 14b.

FIG. 14 is a schematic diagram showing the predicted region of neck 14b.

When a region RH (expressed in a large number of dots) for the neck 14b of the second subject is predicted, a reference position Ka of the region RH is first determined based on the position G1 (refer to FIGS. 11 and 12) of the neck 14b of the first subject. The reference position Ka can be determined by converting the position G1 to the position relative to the scan region RS2, for example.

After the reference position Ka has been determined, a proportion Q of a region RP to the scan region RS2 is determined based on the proportion P (=25%) related to the first subject. The proportion Q can be decided as the same value as the proportion P (=25%) related to the first subject, for example. The region RH can be predicted by determining the reference position Ka and the proportion Q as described above. Incidentally, the region RH of the neck 14b may be defined as one region such as a cone, a cylinder, a sphere, a polyhedron, a columnar body, a rectangular parallelepiped, a cube or the like. Alternatively, it may be defined as a combination of plural regions. After the region RH for the neck 14b has been predicted, the processing flow proceeds to Step S4.

At Step S4, the coil element selection device 113 selects the corresponding combination of coil elements used to receive magnetic resonance signals out of three combinations Set1 through Set3 of coil elements, based on the region RH for the neck 14b, which has been predicted at Step S3. Step S4 will be explained with reference to FIG. 7.

At Substep S41, the coil element selection device 113 first calculates the volumes of overlap regions between respective sensitive regions CR1 through CR3 of the combinations Set1 through Set3 and the region RH.

Figure 15A:
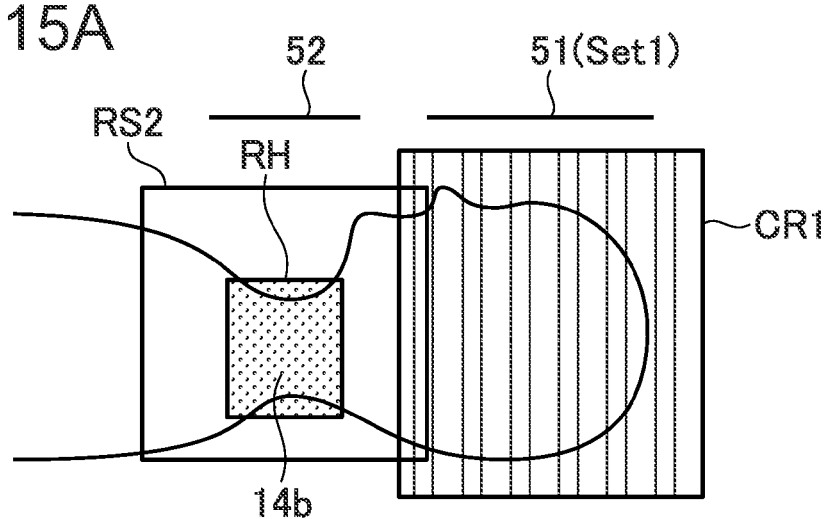
FIGS. 15A, 15B, and 15C are diagrams showing overlap region between sensitive regions CR1 through CR3 of combinations Set1 through Set3 of coil elements and a predicted region RH.
Figure 15B:
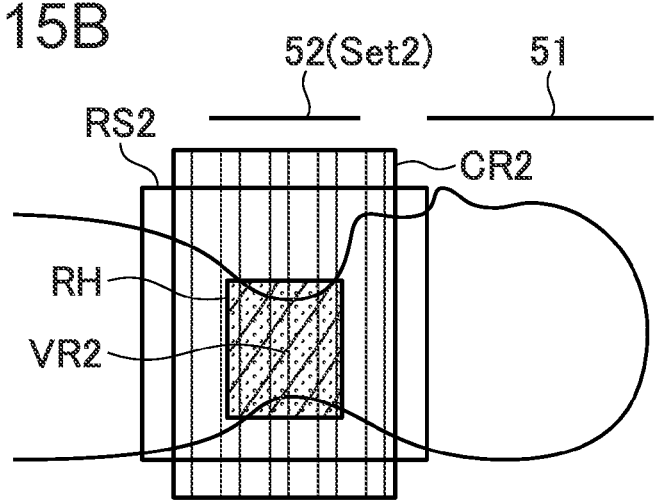
Figure 15C:
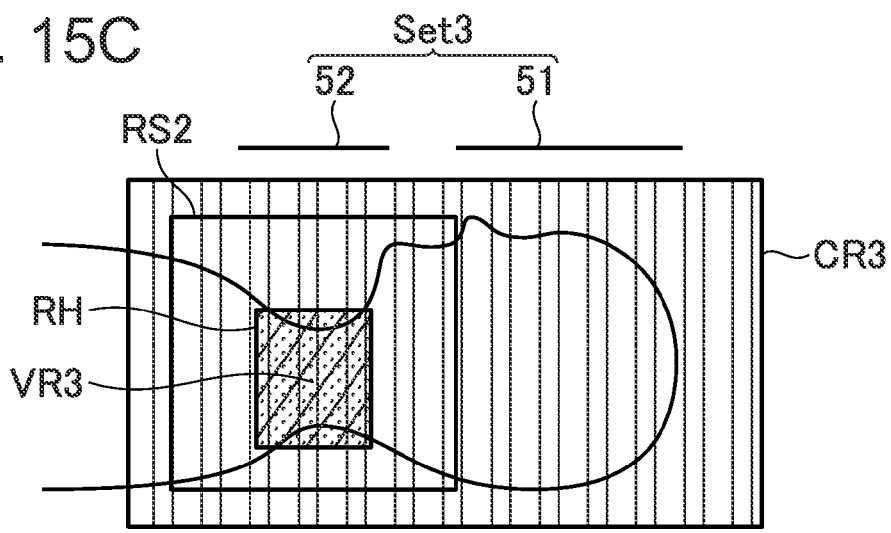

FIGS. 15A-15C are diagrams showing the overlap regions between the sensitive regions CR1 through CR3 of the combinations Set1 through Set3 and the predicted region RH. The overlap regions are represented in diagonal lines in FIG. 15. Incidentally, since the sensitive region CR1 (refer to FIG. 15A) is located outside the predicted region RH of neck 14b, the overlap region does not exist between the sensitive region CR1 and the region RH. Accordingly, only the overlap region VR2 (refer to FIG. 15B) and the overlap region VR3 (refer to FIG. 15C) are shown in FIGS. 15A-15C.

FIG. 16 is a table showing the volumes Vover of the overlap regions VR2 and VR3. For convenience of explanation, the volumes Vover of the overlap regions VR2 and VR3 are represented in the form of characters of v21 and v31 in FIG. 16. Incidentally, since the overlap region does not exist between the sensitive region CR1 and the region RH as shown in FIG. 15A, the volume of the overlap region becomes Vover=00.

After the volumes of the overlap regions have been determined, the flow proceeds to Substep S42.

At Substep S42, the coil element selection device 113 calculates volume rates Cp and Csense, based on the volumes Vover (refer to FIG. 16) of the overlap regions calculated at Substep S41. The volume rates Cp and Csense can be calculated using the above equations (1) and (2). FIG. 17 shows one example illustrative of the values of the volume rates Cp and Csense for each of combinations of the predicted region RH of neck 14b and the sensitive regions CR1 through CR3. Incidentally, since no overlap region exists between the sensitive region CR1 and the region RH, the values of the volume rates Cp and Csense become Cp=0(%) and Csense=0(%) respectively.

After the volume rates Cp and Csense have been calculated, the flow proceeds to Substep S43.

At Substep S43, the coil element selection device 113 selects a candidate for the combination of the coil elements used to receive magnetic resonance signals in the corresponding scan region RS2 from within the combinations Set1 through Set3 (refer to FIG. 15) of the coil elements, based on the value of the volume rate Cp.

As described above, the larger the value of the volume rate Cp, the greater the proportion of overlap of the predicted region RH of neck 14b on each sensitive region. Thus, at Substep S43, the corresponding combination of coil elements, having the sensitive region at the time that the volume rate Cp becomes a maximum value, is selected as a candidate for the combination of the coil elements used to receive the magnetic resonance signals in the scan region RS2. Here, the maximum value of the volume rate Cp is 100(%) (refer to FIG. 17). As shown in FIG. 17, two sensitive regions CR2 and CR3 exist as the sensitive regions at the time of Cp=100(%). Thus, at Substep S43, the following two combinations are selected as candidates for the combinations:

(1) Combination Set2 having sensitive region CR2, and
(2) Combination Set3 having sensitive region CR3

After the combinations Set2 and Set3 have been selected, the flow proceeds to Substep S44.

At Substep S44, the coil element selection device 113 determines whether the candidate for the combination selected at Substep S43 is singular or plural. Since the two candidates are selected here (Set2 and Set3), the flow proceeds to Substep S45.

At Substep S45, the coil element selection device 113 selects the corresponding combination of coil elements used to receive the magnetic resonance signals in the scan region RS2 out of the combinations Set2 and Set3 selected at Substep S43, based on the value of the volume rate Csense. At Substep S45, the combination largest in the volume rate Csense is selected within the combinations Set2 and Set3. As shown in FIG. 17, the volume rate Csense=30(%) at the sensitive region CR2 of the combination Set2, whereas the volume rate Csense=15(%) at the sensitive region CR3 of the combination Set3. Namely, the sensitive region CR2 of the combination Set2 is larger in volume rate Csense rather than the sensitive region CR3 of the combination Set3. Thus, the combination Set2 large in the volume rate Csense out of the combinations Set2 and Set3 is decided as the combination of the coil elements used upon reception of the magnetic resonance signals, and the flow shown in FIG. 7 is terminated. After the corresponding combination has been determined, the processing flow proceeds to Step S5 (refer to FIG. 4).

At Step S5, an imaging scan is carried out using the combination Set2 selected at Step S4. After the imaging scan has been executed, the processing flow proceeds to Step S6.

At Step S6, the calculation device 111 calculates a proportion P of the neck 14b to the scan region RS2 and a position G thereof, based on the magnetic resonance signals acquired by executing the scan at Step S5. The proportion P and position G of the neck 14b can be calculated by a method similar to that used for the first subject. The calculated proportion P and position G are stored in the database 10 in relation to the protocol used when the second subject 14 is imaged (refer to FIG. 18).

FIG. 18 is a conceptual diagram showing the contents stored in the database 10.

A proportion P of the neck 14b to the scan region RS2 of the second subject 14 and a position G thereof are stored in the database 10 in association with the protocol used when the second subject 14 is imaged. Here, the proportion P and position G at the second subject 14 are assumed to be P=26% and G=G2. Since the protocol Px is selected at Step S1 where the second subject 14 is imaged, the proportion P (=26%) and position G (=G2) of the second subject 14 are stored corresponding to the protocol Px.

The flow shown in FIG. 4 is terminated in the above-described manner.

Upon imaging the second subject, the region RH of the neck 14b is predicted from within the scan region RS2, based on the proportion P and position G of the neck 14b both calculated upon the imaging of the first subject carried out in the past. It is thus possible to eliminate most of regions or parts (such as the head and shoulder) other than the neck 14b from the region RH. Since the coil element selection device 113 selects the combination of coil elements, based on the predicted region RH, the corresponding combination of coil elements suitable for the imaging of the neck 14b of the second subject is selected.

Incidentally, FIG. 15 explains where the neck 14b of the subject is located approximately directly below the coil element 52. The position of the neck 14b of the subject may, however, shift from immediately underneath the coil element 52 depending on the height of the subject and imaging conditions. A description will be made below of which combination of coil elements is selected where the position of the neck 14b of the subject shifts from directly beneath the coil element 52, with reference to FIGS. 9 and 20 together with FIG. 7.

Figure 19A:
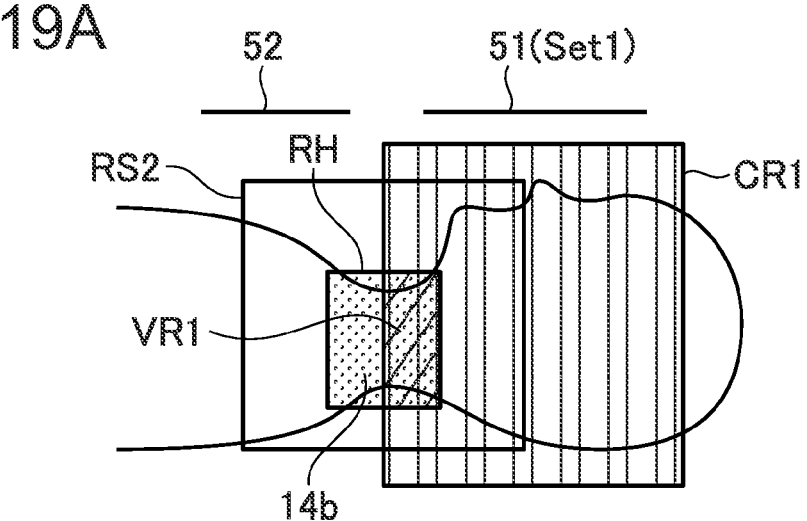
FIGS. 19A, 19B, and 19C are diagrams illustrating a relationship in position between the predicted region RH of neck 14b and the sensitive regions CR1 through CR3 where the position of the neck 14b of the subject is shifted toward the coil element 51 side.
Figure 19B:
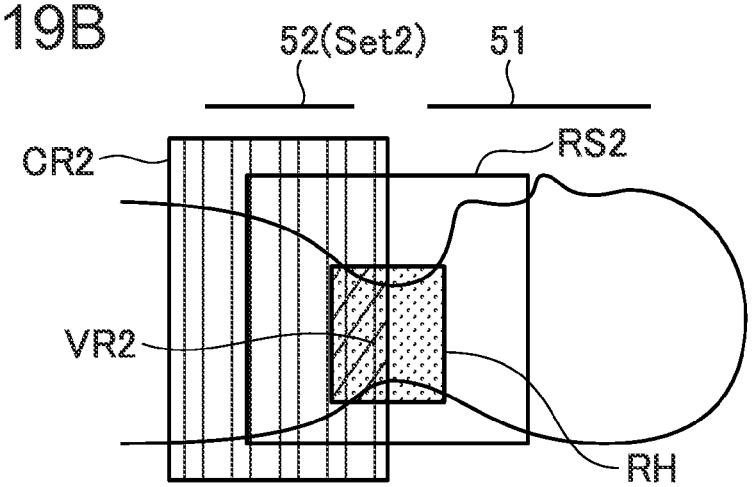
Figure 19C:
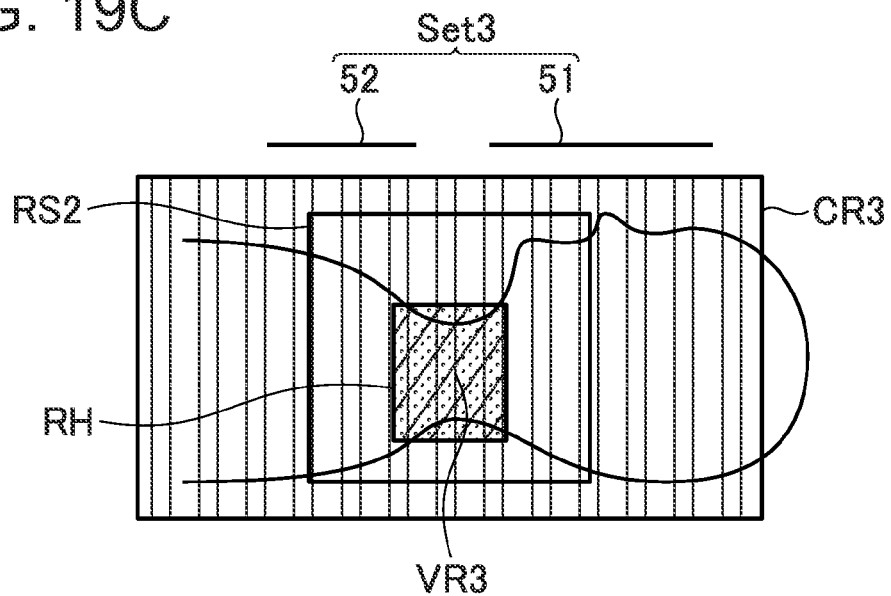

FIGS. 19A-19C are diagrams showing a relationship in position between the predicted region RH of neck 14b and the sensitive regions CR1 through CR3 where the position of the neck 14 of the subject is shifted toward the coil element 51 side. Overlap regions VR1 through VR3 are represented in diagonal lines in FIGS. 19A-19C.

Figures 20, 21:
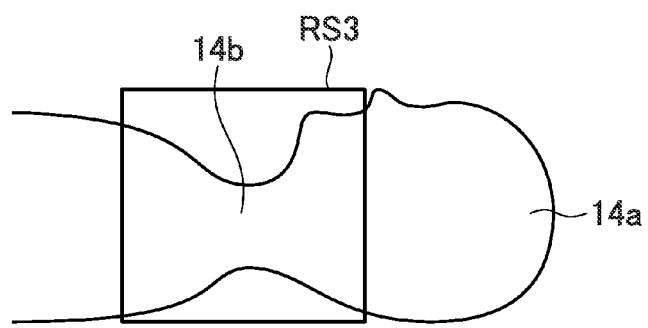
FIG. 20 is a diagram showing one example illustrative of the values of a volume rate Cp and a volume rate Csense.
FIG. 21 is a diagram illustrating a set scan region.

At Substep S41 (refer to FIG. 7), the volumes Vover of the overlap regions VR1 through VR3 are first determined. At Substep S42, a volume rate Cp and a volume rate Csense are calculated. The volume rate Cp and the volume rate Csense can be calculated using the above equations (1) and (2). FIG. 20 shows one example illustrative of the values of the volume rates Cp and Csense for each of combinations of the predicted region RH of neck 14b and the sensitive regions CR1 through CR3.

After the volume rates Cp and Csense have been calculated, the flow proceeds to Substep S43.

At Substep S43, a candidate for the combination of coil elements used to receive magnetic resonance signals in the scan region RS2 is selected out of combinations Set1 through Set3 (refer to FIG. 19) of coil elements, based on the value of each volume rate Cp (refer to FIG. 20). Referring to FIG. 20, the maximum value of the volume rate Cp is 100(%) and the sensitive region at the time that Cp=100(%) is given as the sensitive region CR3. Therefore, at Substep S43, the combination Set3 having the sensitive region CR3 is selected as a candidate for the combination of the coil elements. After the combination Set3 has been selected, the flow proceeds to Substep S44.

At Substep S44, it is determined whether the candidate for the combination selected at Substep S43 is singular or plural. Since only one candidate for the combination (Set3) is selected, the combination Set3 is determined as the corresponding combination of coil elements used when receiving the magnetic resonance signals, and the flow shown in FIG. 7 is terminated.

When the position of the neck 14b of the subject is shifted toward the coil element 51 side as shown in FIGS. 19A-19C, the combination Set2 is not selected but the combination Set3 is selected. It is thus possible to select the optimal combination of coil elements according to the position of the neck 14b of the subject.

After the second subject 14 has been imaged, a third subject 14 is imaged. The imaging of the third subject 14 will also be explained with reference to the flowcharts shown in FIGS. 4 and 7.

At Step S1, the operator 15 selects a protocol used when the third subject 14 is imaged. Assume here that a protocol Px suitable for the imaging of the neck 14b is selected in a manner similar to when the first and second subjects 14 are imaged. After the protocol Px has been selected, the processing flow proceeds to Step S2.

At Step S2, a scan for acquiring image data used upon the setting of a scan region is performed. The scan region is set referring to an MR image obtained by this scan (refer to FIG. 21).

FIG. 21 is a diagram showing the set scan region.

At Step S2, the operator 15 sets a slice position and a slice thickness or the like to thereby set a scan region RS3 taken when the neck 14b of the third subject 14 is scanned. After the scan region RS3 has been set, the processing flow proceeds to Step S3.

At Step S3, the prediction device 112 predicts a region for the neck 14b from within the scan region RS3, based on the rates P and positions G stored in the database 10. In order to predict the region of the neck 14b, it is first determined whether the proportion P and position G associated with the same protocol as the protocol Px selected when the third subject 14 is imaged are stored in the database 10. The proportions P and positions G of the necks 14b stored when the first and second subjects 14 are imaged, have been stored in the database 10 (refer to FIG. 18). Thus it is understood that the protocol Px selected when imaging the third subject 14 is identical to the protocol selected upon imaging the first and second subjects 14. In this case, the corresponding region RH of the neck 14b is predicted from within the scan region RS3, based on the proportion P and position G obtained for the first subject 14, and the proportion P and position G obtained for the second subject 14.

Figures 22, 23:
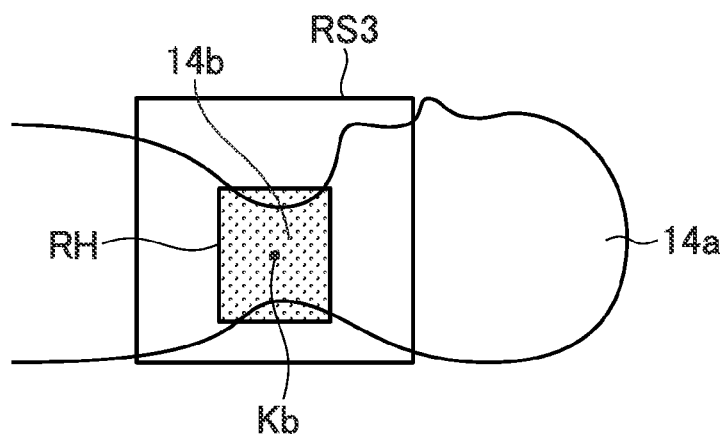
FIG. 22 is a schematic diagram showing a predicted region RH of neck 14b.
FIG. 23 is a conceptual diagram depicting the contents stored in the database 10.

FIG. 22 is a schematic diagram showing the predicted region RH of neck 14b.

When the region RH (expressed in a large number of dots) for the neck 14b of the third subject is predicted, a reference position Kb of the region RH is first determined based on the positions G1 and G2 (refer to FIG. 18) of the necks 14b of the first and second subjects. The reference position Kb can be determined by, for example, converting the positions G1 and G2 to the positions relative to the scan region RS3 and taking the same as an average value of the post-conversion positions G and G2. Only the position G1 or G2 is converted to the position relative to the scan region RS3 and the post-conversion position may be decided as the reference position Kb. Further, the position G1 or G2 is weighted and the reference position Kb may be calculated based on the weighted position.

After the reference position Kb has been determined, a proportion Q of the region RH to the scan region RS3 is determined based on the proportion P (=25%) related to the first subject and the proportion P (=26%) related to the second subject. The proportion Q can be decided as, for example, the same value as the proportion P (=25%) related to the first subject, the same value as the proportion P (=26%) related to the second subject or an average value (25.5%) of 25% and 26%. Further, the proportion P is weighted and the proportion Q of the region RH to the scan region RS3 may be calculated based on the weighted proportion P. The region RH of the neck 14b can be predicted by determining the reference position Kb and the proportion Q as described above. After the region RH of the neck 14b has been predicted, the processing flow proceeds to Step S4.

At Step S4, the coil element selection device 113 selects the corresponding combination of coil elements used to receive the magnetic resonance signals out of the three combinations Sel1 through Set3 (refer to FIG. 3), based on the region RH of the neck 14b predicted at Step S3. Since a method for selecting the corresponding combination of coil elements is identical to the method described up to now, the description of Step S4 will be omitted. After the above combination has been selected, the processing flow proceeds to Step S5.

At Step S5, an imaging scan is performed using the combination selected at Step S4. After the imaging scan has been executed, the processing flow proceeds to Step S6.

At Step S6, a proportion P of the neck 14b to the scan region RS3 and a position G thereof are calculated based on the magnetic resonance signals acquired by executing the scan at Step S5. The proportion P and position G can be calculated by a method similar to that used for the first subject. The calculated proportion P and position G are stored in the database 10 in relation to the protocol used when the third subject 14 is imaged (refer to FIG. 23).

FIG. 23 is a conceptual diagram showing the contents stored in the database 10.

A proportion P of the neck 14b to the scan region RS3 of the third subject 14 and a position G thereof are stored in the database 10 in association with the protocol used when the third subject 14 is imaged. Here, the proportion P and position G at the third subject 14 are assumed to be P=28% and G=G3. Since the protocol Px is selected at Step S1 where the third subject 14 is imaged, the proportion P (=28%) and position G (=G3) of the third subject 14 are stored corresponding to the protocol Px.

The flow shown in FIG. 4 is terminated in the above-described manner.

Subsequently, in the same manner as above, a proportion P and a position G are calculated each time each subject 14 is imaged, and stored corresponding to a protocol.

Figures 24, 25:
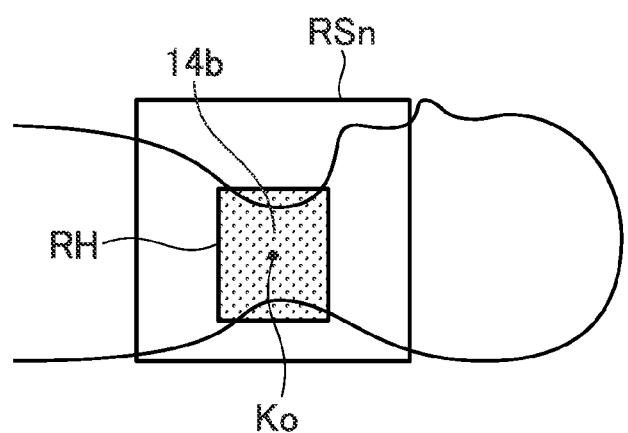
FIG. 24 is a conceptual diagram showing the contents stored in the database 10 when an n−1th subject 14 is imaged.
FIG. 25 is a schematic diagram illustrating a scan region RSn and a predicted region RH of neck 14b at an nth subject.

FIG. 24 is a conceptual diagram showing the contents stored in the database 10 when an n−1th subject 14 is imaged.

Proportions P and positions G related to the first to n−1th subjects are stored in the database 10 in association with each used protocol. In the first embodiment, the proportion P and positions G related to the first to n−1th subjects are assumed to be stored corresponding to the same protocol Px.

After the n−1th subject has been imaged, the nth subject is imaged.

When the nth subject is imaged, a region RH of a neck 14b is predicted based on the proportions P and positions G related to the first to n−1th subjects after a scan region RSn has been set (refer to FIG. 25).

FIG. 25 is a schematic diagram showing the scan region RSn and the predicted region RH of neck 14b at the nth subject.

When the region RH (expressed in a large number of dots) of the neck 14b of the nth subject is predicted, a reference position K0 of the region RH is first determined based on the positions G1 through $G_{n-1}$ (refer to FIG. 24) of the necks 14b of the first through n−1th subjects. The reference position K0 can be determined by, for example, converting the positions G1 through $G_{n-1}$ to the positions relative to the scan region RSn and taking the same as an average value of the post-conversion positions G through $G_{n-1}$. One or more positions are selected from within the positions Gn through $G_{n-1}$, and the reference position Kb may be determined based on the selected positions. Further, the positions G1 through $G_{n-1}$ are weighted and the reference position K0 may be calculated based on the weighted positions G1 through $G_{n-1}$.

After the reference position K0 has been determined, a proportion Q of the region RH to the scan region RSn is determined based on the proportions P related to the first to n−1th subjects. The proportion Q can be decided as, for example, an average value of the proportions P related to the first through n−1th subjects. Incidentally, each proportion P is weighted and the proportion Q of the region RH relative to the scan region RSn may be calculated based on the weighted proportion P. After the region RH of the neck 14b has been predicted, the corresponding combination of coil elements is selected by a similar procedure and an imaging scan is performed based on the same. After the imaging scan has been executed, the proportion P of the neck 14b to the scan region RSn and the position G of the neck 14b are calculated. The proportion P and position G can be calculated by a method similar to that for the first subject. The calculated proportion P and position G are stored in the database 10 in relation to the corresponding protocol used when the nth subject 14 is imaged (refer to FIG. 26).

FIG. 26 is a conceptual diagram showing the contents stored in the database 10.

The proportion P and position G of the neck 14b relative to the scan region RSn of the nth subject 14 are stored in the database 10 in association with the protocol Px used when the nth subject 14 is imaged. Here, the proportion P and position G at the nth subject 14 are P=28% and G=Gn respectively.

When imaging the nth subject, the corresponding region RH of neck 14b is predicted from within the scan region RSn, based on the proportions P and positions G of the necks 14b, which have been calculated upon the previously-performed imaging of first through n−1th subjects. It is thus possible to eliminate most of regions or parts (such as the head and shoulder) other than the neck 14b from the region RH. Therefore, the corresponding combination of coil elements suitable for the imaging of the neck 14b of the nth subject can be selected.

In the first embodiment, the position G of each neck has been stored as the position relative to the scan region. The position G of the neck is not necessarily required to be stored as the position relative to the scan region. The position thereof may be stored as, for example, a position relative to the receiving coil 5.

Incidentally, the scan region may be defined as one region such as a cone, a cylinder, a sphere, a polyhedron, a columnar body, a rectangular parallelepiped, a cube or the like. Alternatively, it may be defined as a combination of plural regions different in shape.

(2) Second Embodiment

In the first embodiment, the proportions P and positions G calculated at Step S6 have been stored corresponding to the used protocol. A second embodiment will explain the case where the proportion P and position G calculated at Step S6 are stored in association not only with the used protocol but also with information about each subject 14.

FIG. 27 is a conceptual diagram showing data stored in the database 10 in the second embodiment.

In the second embodiment, the proportion P and position G calculated at Step S6 are stored in association not only with the used protocol but also with the information (height in the second embodiment) about each subject 14. The calculated proportion P and position G can be weighted according to the height of each subject 14 by associating the proportion P and position G with the height thereof. It is thus possible to reduce a displacement in position between an actual region of a neck 14b and a predicted region RH of neck 14b and select a more suitable combination of coil elements.

When the proportions P and positions G are retrieved from within the database 10, only the proportions P and positions G obtained when the subjects 14 approximately identical in height may be retrieved. A decision as to whether they are identical in height is performed as follows. For instance, it may be determined that they are identical in height where the difference in height therebetween falls within a predetermined range. It may be determined that they are different in height where the difference in height therebetween is beyond the predetermined range. In this case, the region for each neck 14b is predicted based on the proportions P and positions G obtained when the subjects 14 approximately identical in height are imaged. Thus, even though the proportion P of the neck 14b of each subject 14 differs greatly depending on the height of the subject 14, the region for the neck 14b can be predicted according to the height of the subject 14. It is therefore possible to select an optimal combination of coil elements.

Incidentally, when the proportion P of the neck 14b of each subject 14 differs greatly depending on the boy weight of the subject 14, the proportions P and positions G calculated as Step S6 may be stored corresponding to the body weight or may be stored corresponding to both the weight and height.

(3) Third Embodiment

Although the first and second embodiment have explained the case where each subject is imaged using the protocol Px suitable for the imaging of the neck, a third embodiment will explain a case where a subject is imaged using a protocol Py suitable for the imaging of each breast.

Figure 28:
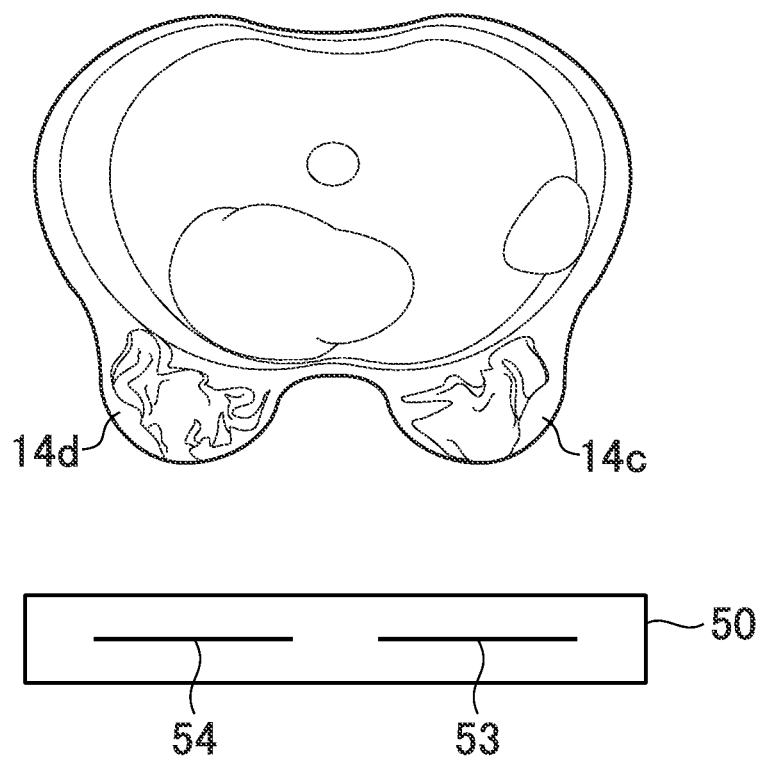
FIG. 28 is a diagram for describing a receiving coil used for imaging of each breast in a third embodiment.

FIG. 28 is a diagram for describing a receiving coil used for the imaging of the breast.

Incidentally, the cross-section or plane of a subject shown in FIG. 28 is of an axial plane.

The receiving coil 50 receives magnetic resonance signals of breasts 14c and 14d of the subject. The receiving coil 50 has a plurality of coil elements. Although only two coil elements 53 and 54 are shown in FIG. 28 as coil elements included in the receiving coil 5, the receiving coil 5 actually has more coil elements. For convenience of explanation, however, the receiving coil 50 will be explained below assuming that it has the two coil elements 53 and 54 alone.

When the magnetic resonance signals are received from the subject 14, the corresponding combination of coil elements suitable for receiving the magnetic resonance signals of the subject 14 is selected from within the two coil elements 53 and 54. In the third embodiment, three combinations Set1, Set12 and Set13 of coil elements are selectable. The combinations Set11, Set12 and Set13 thereof are as follows:

Set11=coil element 53
Set12=coil element 54
Set13=coil element 53+coil element 54

Namely, the combination Set11 is comprised of the coil element 53, and the combination Set12 is comprised of the coil element 54. Further, the combination Set13 is comprised of the coil elements 53 and 54.

Sensitive regions of the combinations Set11 through Set13 of the coil elements will next be explained.

Figure 29A:
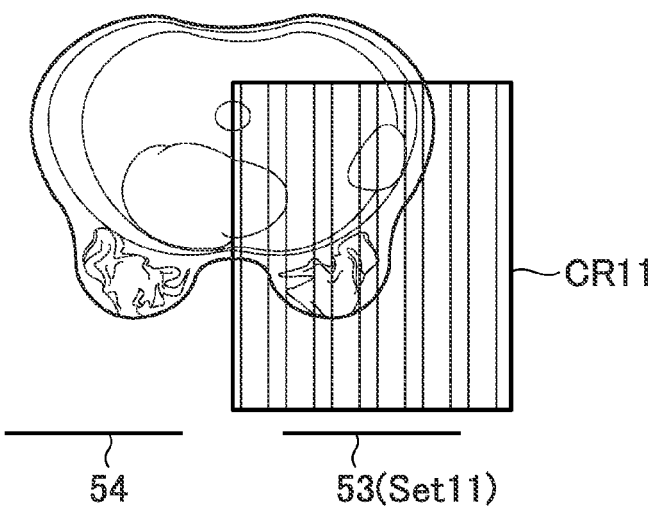
FIGS. 29A, 29B, and 29C are diagrams for explaining sensitive regions of combinations Set11 through Set13 of coil elements.
Figure 29B:
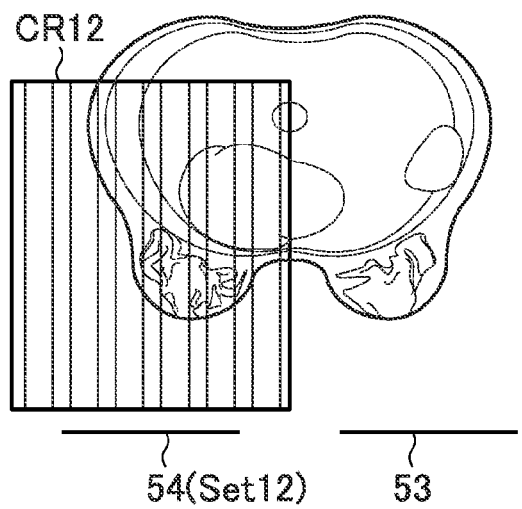
Figure 29C:
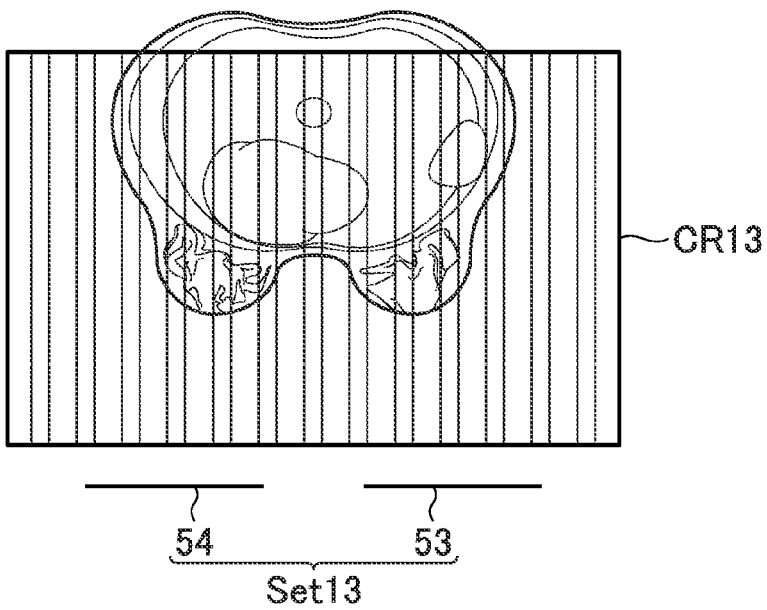

FIGS. 29A-29C are diagrams for describing the sensitive regions of the combinations Set11 through Set13.

FIGS. 29A through 29C respectively show the sensitive regions CR11 through CR13 (hatched portions) of the combinations Set11 through Set13. For example, the sensitive region CR11 (refer to FIGS. 29A-29C) is a region in which the combination Set11 is considered to have sensitivity enough to obtain a high-quality MR image. The extent of the sensitive region CR11 is determined based on a sensitivity characteristic of the combination Set11, which has been examined in advance. Information (position information about the sensitive region CR11, the volume of the sensitive region CR11, etc.) about the sensitive region CR11 has been stored in the database 10.

Although the above description has been made of the sensitive region CR11 of the combination Set11, the sensitive regions CR12 and CR13 of other combinations Set12 and Set13 are also similar to the above.

The sensitive regions CR11 through CR13 of the combinations Set11 through Set13 are defined as described above.

A processing flow of the MRI apparatus 1 will next be described with reference to FIGS. 4 and 7. Incidentally, in the following description, proportions P and positions G related to n subjects (refer to FIG. 26) are assumed to have been stored in the database 10.

At Step S1, the operator 15 installs the receiving coil 50 (refer to FIG. 28) to an n+1th subject 14 and selects a protocol used when the n+1th subject 14 is imaged. Since the breasts are imaged in the third embodiment, the operator 15 selects a protocol Py suitable for the imaging of the breasts. After the protocol has been selected, the processing flow proceeds to Step S2.

At Step S2, a scan for acquiring image data used upon the setting of a scan region is performed. The scan region is set referring to an MR image obtained by this scan (refer to FIG. 30).

Figure 30:
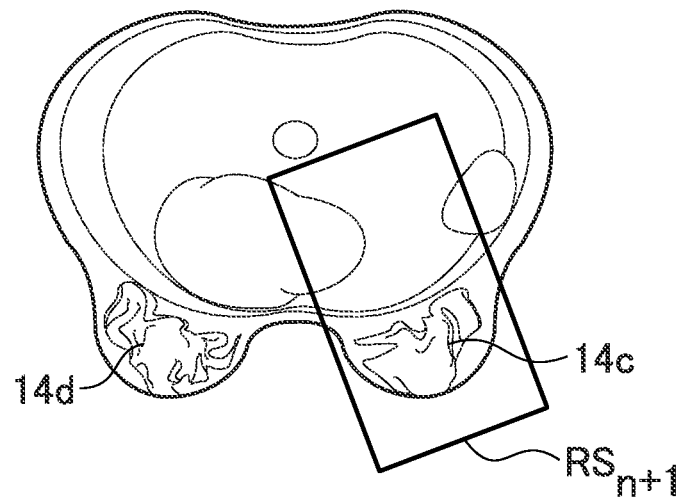
FIG. 30 is a diagram showing a set scan region.

FIG. 30 is a diagram showing the set scan region.

At Step S2, the operator 15 sets a slice position and a slice thickness or the like to thereby set a scan region $RS_{n+1}$ taken when the breast 14c of the n+1th subject is scanned. After the scan region $RS_{n+1}$ has been set, the processing flow proceeds to Step S3.

Figure 31:
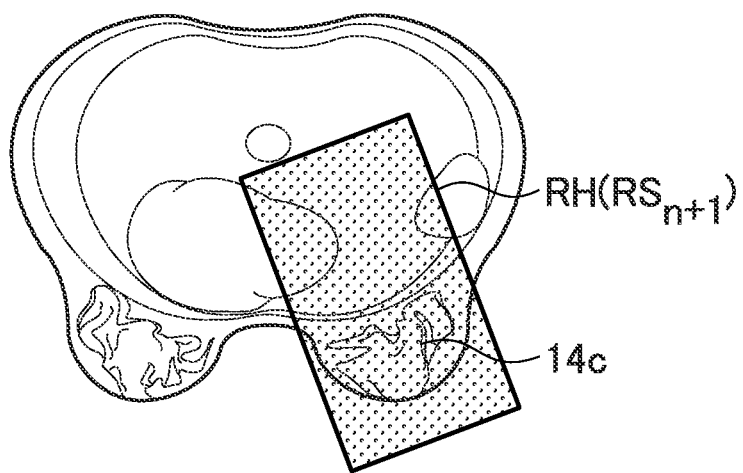
FIG. 31 is a diagram illustrating a predicted region RH of breast 14c.

At Step S3, the prediction device 112 predicts the region of the breast 14c from within the scan region $RS_{n+1}$, based on the proportions P and positions G (refer to FIG. 26) stored in the database 10. In order to predict the region for the breast 14c, it is first determined whether a proportion P and a position G associated with the same protocol as the protocol Py selected when the n+1th subject 14 is imaged are stored in the database 10. The proportions P and positions G obtained when the first through nth subjects 14 are imaged have been stored in the database 10. Since, however, the proportions P and positions G stored in the database 10 are associated with the protocol Px suitable for the imaging of the necks, the proportions P and positions G associated with the protocol Py suitable for the imaging of the breasts are not stored in the database 10. Accordingly, 100% (whole of scan region $RS_{n+1}$) of the scan region $RS_{n+1}$ is predicted as a region RH of the breast 14c. The predicted region RH of breast 14c is expressed in a large number of dots in FIG. 31. It is understood that referring to FIG. 31, the scan region $RS_{n+1}$ coincides with the predicted region RH of breast 14c. After the region RH of the breast 14c has been predicted, the processing flow proceeds to Step S4.

At Step S4, the coil element selection device 113 selects the corresponding combination of coil elements used to receive each magnetic resonance signal from within the three combinations Set11 through Set13, based on the region RH of the breast 14c predicted at Step S3. Step S4 will be explained with reference to FIG. 7.

At Substep S41, the coil element selection device 113 first calculates the volumes of overlap regions between the sensitive regions CR11 through CR13 of the combinations Set11 through Set13 of the coil elements and the region RH.

Figure 32A:
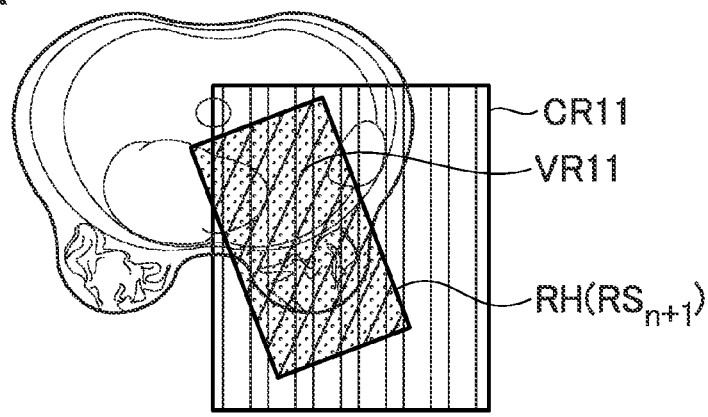
FIGS. 32A, 32B, and 32C are diagrams showing overlap regions VR11 through VR13 between the sensitive regions CR11 through CR13 of the combinations Set11 through Set13 of the coil elements and a predicted region RH.
Figure 32B:
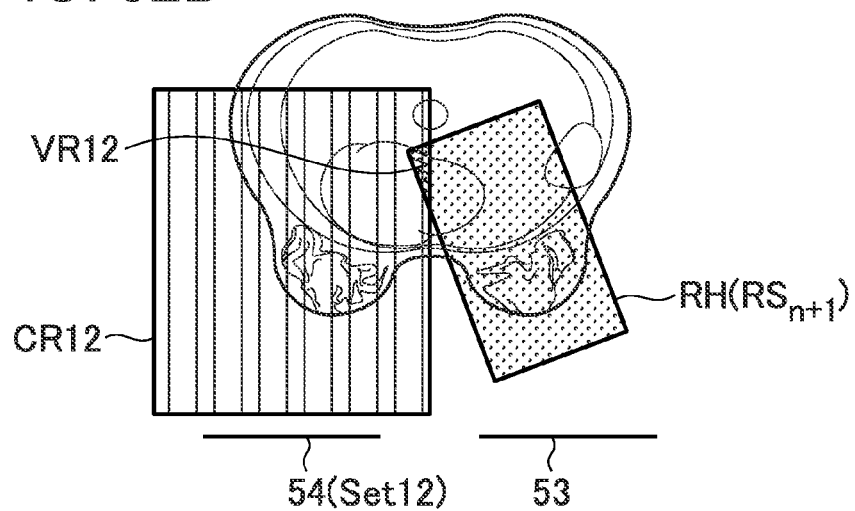
Figure 32C:
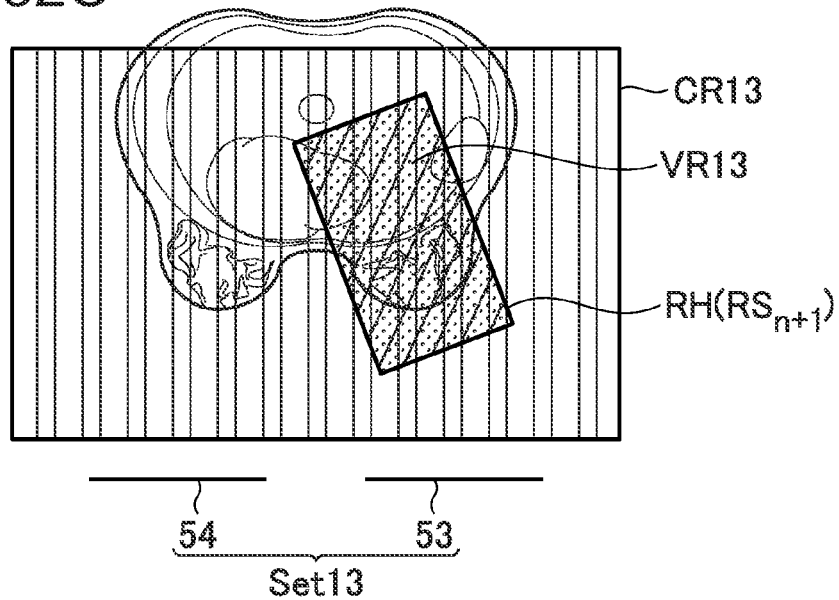

FIGS. 32A-32C are diagrams showing the overlap regions VR11 through VR13 between the sensitive regions CR11 through CR13 of the combinations Set11 through Set13 and the predicted region RH. The overlap regions VR11 through VR13 are represented in diagonal lines in FIGS. 32A-32C.

Figures 33, 34:
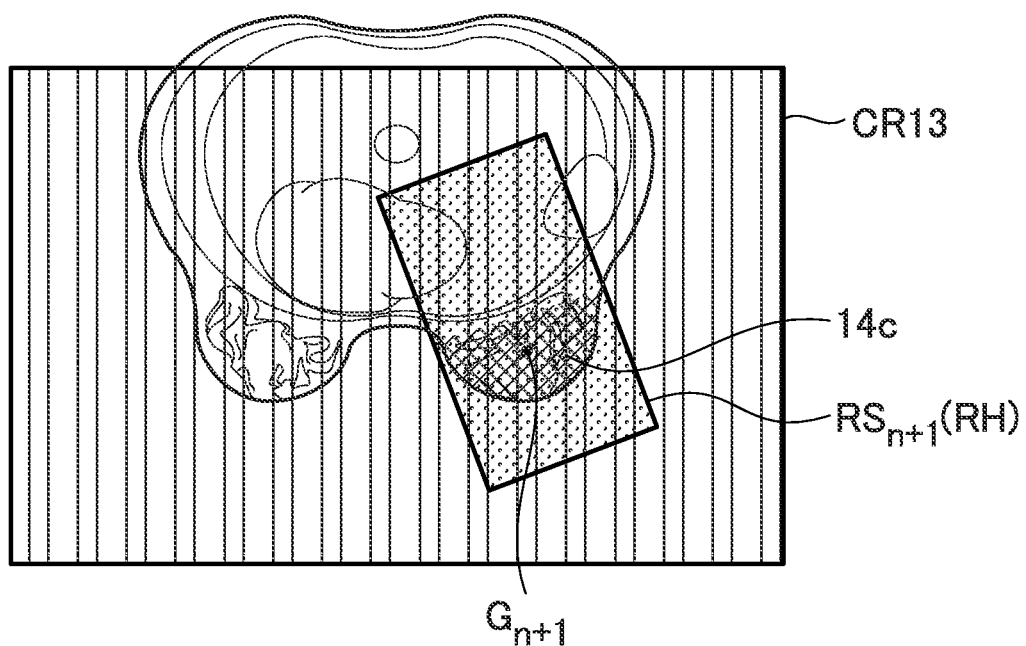
FIG. 33 shows one example illustrative of the values of a volume rate Cp and a volume rate Csense.
FIG. 34 is a diagram showing a breast 14c extracted from within a scan region RSn+1.

After the volumes of the overlap regions VR11 through VR13 have been determined, the flow proceeds to Substep S42, where a volume rate Cp and a volume rate Csense are calculated. The volume rate Cp and the volume rate Csense can be calculated by a method similar to that employed in the first embodiment. One example illustrative of the values of the volume rate Cp and the volume rate Csense is shown in FIG. 33 for each of the combinations of the predicted region RH of breast 14c and the sensitive regions CR11 through CR13.

After the volume rate Cp and the volume rate Csense have been calculated, the flow proceeds to Substep S43.

At Substep S43, the coil element selection device 113 selects a candidate for the corresponding combination of coil elements used to receive magnetic resonance signals in the scan region $RS_{n+1}$ out of the combinations Set11 through Set13 (refer to FIGS. 32A-32C), based on the value of each volume rate Cp.

As described in the first embodiment, the larger the value of the volume rate Cp, the greater the proportion of overlap of the predicted region RH on each sensitive region. Thus, at Substep S43, the combination of coil elements, having the sensitive region at the time that the volume rate Cp becomes a maximum value, is selected as a candidate for the combination of the coil elements used to receive the magnetic resonance signals in the scan region $RS_{n+1}$. Here, the maximum value of the volume rate Cp is 100(%) (refer to FIG. 33). Since the sensitive region at the time that Cp=100(%) corresponds to the sensitive region CR13, the combination Set13 having the sensitive region CR13 is selected as a candidate for the corresponding combination of coil elements at Substep S43. After the combination Set13 has been selected, the flow proceeds to Substep S44.

At Substep S44, the coil element selection device 113 determines whether the candidate for the combination selected at Substep S43 is singular or plural. Since only one candidate for the combination is selected here, the combination Set13 is decided as the combination of the coil elements used when receiving each magnetic resonance signal, and the flow shown in FIG. 7 is terminated. After the corresponding combination of coil elements has been determined, the processing flow proceeds to Step S5 (refer to FIG. 4).

At Step S5, an imaging scan is carried out using the combination Set13 selected at Step S4. After the imaging scan has been executed, the processing flow proceeds to Step S6.

At Step S6, the calculation device 111 calculates a proportion P of the breast 14c to the scan region $RS_{n+1}$ and a position G of the breast 14c, based on the magnetic resonance signals acquired by executing the scan at Step S5. In order to calculate the proportion P of the breast 14c and the position G thereof, the calculation device first extracts the breast 14c from within the scan region $RS_{n+1}$ (refer to FIG. 34).

FIG. 34 is a diagram showing the breast 14c extracted from within the scan region $RS_{n+1}$.

The extracted breast 14c is shown cross-hatched in FIG. 34. It is possible to calculate a proportion P of the breast 14c to the scan region $RS_{n+1}$ and a position G of the breast 14c by extracting the breast 14c of an n+1th subject 14. Assume here that the proportion P=20% and the position G=Gn+1. The calculated proportion P and position G of breast 14c are stored in the database 10 in relation to the protocol used when the n+1th subject 14 is imaged (refer to FIG. 35).

FIG. 35 is a conceptual diagram showing the contents stored in the database 10.

The proportion P of the breast 14c to the scan region $RS_{n+1}$ of the n+1th subject 14 and the position G thereof are stored in the database 10, corresponding to the protocol used when the n+1th subject 14 is imaged. Since the protocol Py is selected at Step S1 where the n+1th subject 14 is imaged, the proportion P and position G of the n+1th subject 14 are stored corresponding to the protocol Py.

The processing flow shown in FIG. 4 is terminated in the above-described manner.

After the n+1th subject 14 has been imaged, an n+2th subject 14 is imaged. The imaging of the n+2th subject 14 will also be explained with reference to the flowcharts shown in FIGS. 4 and 7.

At Step S1, the operator 15 installs the receiving coil 50 (refer to FIG. 28) on the n+2th subject 14. The operator 15 selects a protocol used when the n+2th subject 14 is imaged. A protocol Py suitable for the imaging of the breasts is selected even with respect to the n+2th subject. After the protocol Py has been selected, the processing flow proceeds to Step S2.

At Step S2, a scan for acquiring image data used when setting the scan region is performed. Then the scan region is set referring to an MR image obtained by this scan (refer to FIG. 36).

Figure 36:
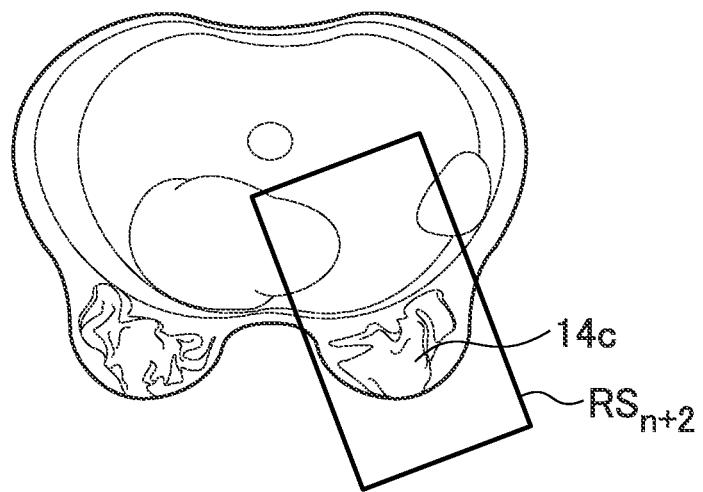
FIG. 36 is a diagram depicting a set scan region.

FIG. 36 is a diagram showing the set scan region.

At Step S2, the operator 15 sets a slice position and a slice thickness or the like to thereby set a scan region $RS_{n+2}$ taken when the breast 14c of the n+2th subject 14 is scanned. After the scan region $RS_{n+2}$ has been set, the processing flow proceeds to Step S3.

At Step S3, the prediction device 112 predicts the region for the breast 14c from within the scan region $RS_{n+2}$, based on the proportions P and positions G stored in the database 10. In order to predict the region of the breast 14c, the prediction device 112 first determines whether a proportion P and a position G associated with the same protocol as the protocol Py selected when the n+2th subject 14 is imaged, are stored in the database 10. The proportion P and the position G of the breast 14c, which have been stored when the n+1th subject 14 is imaged, have been stored in the database 10 in association with the protocol Py (refer to FIG. 35). Thus, the protocol Py selected when imaging the n+2th subject 14 is identical to the protocol selected upon imaging the n+1th subject 14. In this case, a region RH for the breast 14c is predicted from within the scan region $RS_{n+2}$ on the basis of the proportion P (=20%) and position G (=Gn+1) of the breast 14c both stored in the database 10.

Figure 37:
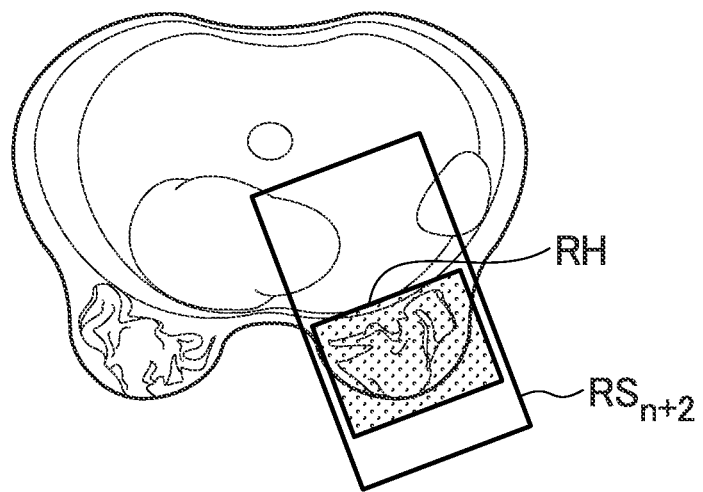
FIG. 37 is a schematic diagram showing a predicted region of breast 14c.

FIG. 37 is a schematic diagram showing the predicted region RH of breast 14c.

The region RH (represented in a large number of dots) of the breast 14c can be predicted by a method similar to the method used when the region of the neck 14b is predicted in the first embodiment. After the region RH of the breast 14c has been predicted, the processing flow proceeds to Step S4.

At Step S4, the coil element selection device 113 selects the corresponding combination of coil elements used to receive magnetic resonance signals out of three combinations Set11 through Set13 of coil elements, based on the region RH for the breast 14c, which has been predicted at Step S3. Step S4 will be explained with reference to FIG. 7.

At Substep S41, the coil element selection device 113 first calculates the volumes of overlap regions between respective sensitive regions CR11 through CTR13 of the combinations Set11 through Set13 and the region RH.

Figure 38A:
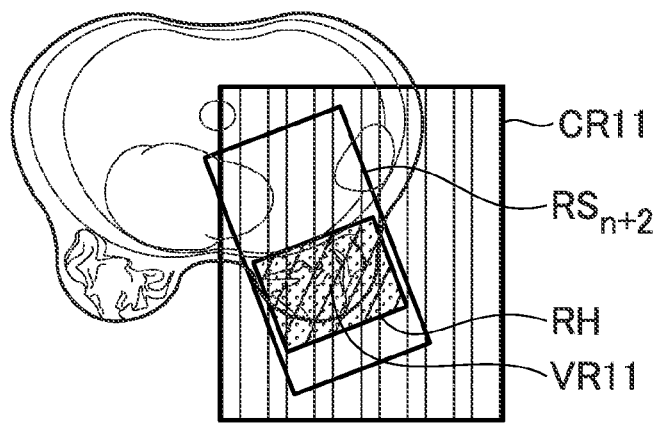
FIGS. 38A, 38B, and 38C are diagrams illustrating overlap regions between the sensitive regions CR11 through CR13 of the combinations Set11 through Set13 of the coil elements and a predicted region RH.
Figure 38B:
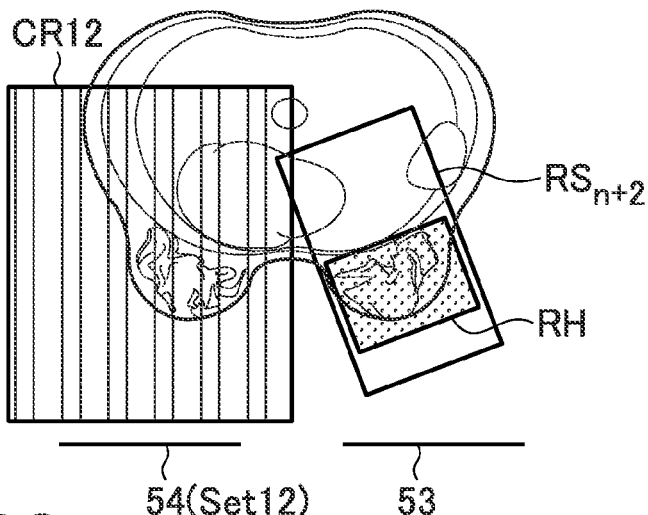
Figure 38C:
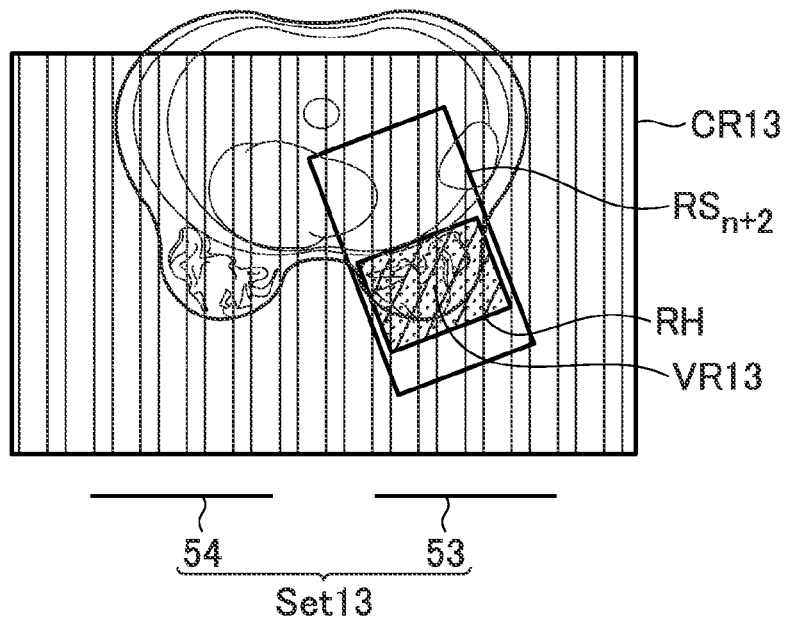

FIGS. 38A-38C are diagrams showing the overlap regions between the sensitive regions CR11 through CR13 of the combinations Set11 through Set13 and the predicted region RH. The overlap regions are represented in diagonal lines in FIGS. 38A-38C. Incidentally, since the sensitive region CR12 (refer to FIG. 38B) is located outside the predicted region RH of breast 14c, the overlap region does not exist between the sensitive region CR12 and the region RH. Accordingly, only the overlap region VR11 (refer to FIG. 38A) and the overlap region VR13 (refer to FIG. 38C) are shown in FIGS. 38A-38C.

After the volumes of the overlap regions have been determined, the flow proceeds to Substep S42, where a volume rate Cp and a volume rate Csense are calculated. The volume rate Cp and the volume rate Csense can be calculated by a method similar to that employed in the first embodiment. One example illustrative of the values of the volume rate Cp and the volume rate Csense is shown in FIG. 39 for each of the combinations of the predicted region RH of breast 14c and the sensitive regions CR11 through CR13. Incidentally, since no overlap region exists in the case of the sensitive region CR12 and the region RH, the values of the volume rate Cp and the volume rate Csense become Cp=0(%) and Csense=0(%) respectively.

After the volume rate Cp and the volume rate Csense have been calculated, the flow proceeds to Substep S43.

At Substep S43, the coil element selection device 113 selects a candidate for the corresponding combination of coil elements used to receive magnetic resonance signals in the scan region $RS_{n+2}$ out of the combinations Set11 through Set13 (refer to FIGS. 38A-38C), based on the value of each volume rate Cp. The selected candidate for the combination corresponds to the combination of the coil elements, having the sensitive region at the time that the volume rate Cp reaches the maximum value. Here, the maximum value of the volume rate Cp is 100(%) (refer to FIG. 39). As shown in FIG. 39, the two sensitive regions CR11 and CR13 exist as the sensitive regions at the time of Cp=100(%). Thus, at Substep S43, the following two combinations are selected as candidates for the combinations:

(1) Combination Set11 having sensitive region CR11, and
(2) Combination Set13 having sensitive region CR13

After the combinations Set11 and Set13 have been selected, the flow proceeds to Substep S44.

At Substep S44, the coil element selection device 113 determines whether the candidate for the combination selected at Substep S43 is singular or plural. Since the two candidates are selected here (Set11 and Set13), the flow proceeds to Substep S45.

At Substep S45, the coil element selection device 113 selects the corresponding combination of coil elements used to receive the magnetic resonance signals in the scan region $RS_{n+2}$ out of the combinations Set11 and Set13 selected at Substep S43, based on the value of each volume rate Csense. At Substep S45, the combination largest in the volume rate Csense is selected within the combinations Set11 and Set13. As shown in FIG. 39, the sensitive region CR11 of the combination Set11 corresponds to the volume rate Csense=15 (%), whereas the sensitive region CR13 of the combination Set13 corresponds to the volume rate Csense=7(%). Namely, the sensitive region CR11 of the combination Set11 is larger in volume rate Csense rather than the sensitive region CR13 of the combination Set13. Thus, the combination Set11 large in the volume rate Csense out of the combinations Set11 and Set13 is decided as the combination of the coil elements used upon reception of the magnetic resonance signals, and the flow shown in FIG. 7 is terminated. After the corresponding combination has been determined, the processing flow proceeds to Step S5 (refer to FIG. 4).

At Step S5, an imaging scan is carried out using the combination Set11 selected at Step S4. After the imaging scan has been executed, the processing flow proceeds to Step S6.

At Step S6, the calculation device 111 calculates a proportion P of the breast 14c to the scan region $RS_{n+2}$ and a position thereof, based on the magnetic resonance signals acquired by executing the scan at Step S5. The proportion P and position G of the breast 14c can be calculated by a method similar to that used for the n+1th subject. The calculated proportion P and position G are stored in the database 10 in relation to the protocol used when the n+2th subject 14 is imaged, and the processing flow shown in FIG. 4 is terminated.

Each of the breasts of the next subject is imaged subsequently in the same manner as above. When each of the breasts of an n+jth subject is imaged, a region RH of each of the breasts of the n+jth subject is predicted based on the proportions P and positions G related to the nth through n+(j−1)th subjects, and the corresponding combination of coil elements may be selected. It is thus possible to select the corresponding combination of coil elements suitable for imaging each breast of the subject with high quality.

Incidentally, in the third embodiment, the proportion P and position G calculated at Step S6 have been stored corresponding to the used protocol. The proportion P and position G calculated at Step S6 may, however, be stored in association not only with the used protocol but also with the chest of each subject 14. The calculated proportion P and position G are associated with the chest of each subject 14, thereby making it possible to weight the proportion P and position G according to the chest of each subject 14. It is thus possible to reduce a displacement in position between an actual region of breast 14c and a predicted region RH of breast 14c and select an optimal combination of coil elements. In this case, when the proportions P and positions G are retrieved from within the database 10, only the proportions P and positions G obtained when the subjects 14 almost identical in chest to each other are imaged may be retrieved. The region of each breast is predicted based on the proportions P and positions G obtained when the subjects 14 almost identical in chest to each other are imaged, thereby making it possible to reduce a displacement in position between an actual region of breast and the predicted region RH of breast and select an optimal combination of coil elements.

Although the above embodiment has explained the example in which the neck or breast is imaged, the invention can be applied even to a case in which other parts or regions other than the neck and breasts are imaged.

Incidentally, the operator 15 may manually change the corresponding combination of coil elements automatically selected at Step S4 to another combination of coil elements. In this case, another combination of coil elements selected by the operator 15 is stored in the database 10 in association with the protocol or information about each subject. When the operator 15 changes the combination of coil elements beyond a predetermined frequency, the operator may use the manually-selected combination of coil elements from the next imaging of subject.

Many widely different embodiments of the invention may be configured without departing from the spirit and the scope of the present invention. It should be understood that the present invention is not limited to the specific embodiments described in the specification, except as defined in the appended claims.

What is claimed is:

1. A magnetic resonance imaging (MRI) apparatus configured to scan a predetermined part of a first subject and a second subject to acquire magnetic resonance signals, said MRI apparatus comprising:
   a plurality of coil elements;
   a calculation device configured to:
      calculate a proportion of a scanned area of the predetermined part to an area of a first scan region of the first subject; and
         calculate a position of the predetermined part within the first scan region based on magnetic resonance signals acquired from scanning the first scan region;
   a prediction device configured to predict a location of the predetermined part within a second scan region of the second subject based on the proportion and the position of the predetermined part calculated for the first subject; and
   a coil element selection device configured to select at least one coil element of the plurality of coil elements used to receive each of a plurality of magnetic resonance signals in the second scan region of the second subject based on the predicted location of the predetermined part within the second scan region.

2. The magnetic resonance imaging apparatus according to claim 1, further comprising a storage device configured to store the proportion and the position of the predetermined part calculated for the first subject.

3. The magnetic resonance imaging apparatus according to claim 2, wherein the storage device is configured to store the proportion and the position of the predetermined part calculated for the first subject in association with a first protocol used when the first subject is imaged.

4. The magnetic resonance imaging apparatus according to claim 3, wherein the first protocol defines a type of a scan executed to image the first subject.

5. The magnetic resonance imaging apparatus according to claim 4, wherein when the first protocol is identical to a second protocol used when the second subject is imaged, the prediction device is configured to predict the location of the predetermined part within the second scan region based on the position of the predetermined part stored in the storage device corresponding to the first protocol.

6. The magnetic resonance imaging apparatus according to claim 5, wherein the storage device is configured to store the proportion and the position of the predetermined part calculated for the first subject in association with physical characteristic information about the first subject.

7. The magnetic resonance imaging apparatus according to claim 4, wherein the storage device is configured to store the proportion and the position of the predetermined part calculated for the first subject in association with physical characteristic information about the first subject.

8. The magnetic resonance imaging apparatus according to claim 4, wherein a plurality of combinations of the plurality of coil elements is selectable from within the plurality of coil elements.

9. The magnetic resonance imaging apparatus according to claim 3, wherein the storage device is configured to store the proportion and the position of the predetermined part calculated for the first subject in association with physical characteristic information about the first subject.

10. The magnetic resonance imaging apparatus according to claim 3, wherein a plurality of combinations of the plurality of coil elements is selectable from within the plurality of coil elements.

11. The magnetic resonance imaging apparatus according to claim 2, wherein the storage device is configured to store the proportion and the position of the predetermined part calculated for the first subject in association with physical characteristic information about the first subject.

12. The magnetic resonance imaging apparatus according to claim 2, wherein a plurality of combinations of the plurality of coil elements is selectable from within the plurality of coil elements.

13. The magnetic resonance imaging apparatus according to claim 1, further comprising a storage device configured to store the proportion and the position of the predetermined part calculated for the first subject in association with physical characteristic information about the first subject.

14. The magnetic resonance imaging apparatus according to claim 13, wherein when the physical characteristic information about the first subject is identical to physical characteristic information about the second subject, the prediction device is configured to predict the location of the predetermined part within the second scan region based on the proportion and the position of the predetermined part both stored in the storage device corresponding to the physical characteristic information about the first subject.

15. The magnetic resonance imaging apparatus according to claim 14, wherein the physical characteristic information about the first subject and the physical characteristic information about the second subject are respectively indicative of a height, a body weight, or a chest proportion or position.

16. The magnetic resonance imaging apparatus according to claim 1, wherein a plurality of combinations of the plurality of coil elements is selectable from within the plurality of coil elements.

17. The magnetic resonance imaging apparatus according to claim 16, wherein a plurality of sensitive regions of the respective combinations of the plurality of coil elements are stored, wherein a sensitive region includes a region in which a combination of coil elements has a sufficient sensitivity to obtain magnetic resonance signals.

18. The magnetic resonance imaging apparatus according to claim 17, wherein the coil element selection device is configured to:
   determine a plurality of overlap regions between the location predicted by the prediction device and the sensitive regions;
   calculate a first volume rate indicative of a proportion of each of the overlap regions to the location predicted by the prediction device and a second volume rate indicative of a proportion of each of the overlap regions to each of the sensitive regions; and
   select a corresponding combination of coil elements used to receive the magnetic resonance signals in the second scan region out of the plurality of combinations of coil elements based on the first volume rate and the second volume rate.

19. The magnetic resonance imaging apparatus according to 18, wherein the coil element selection device is configured to select a first combination of coil elements used to receive the magnetic resonance signals in the second scan region from the plurality of combinations of coil elements based on the first volume rate, and to select, when the first combination exists in plural form, a corresponding combination of coil elements used to receive the magnetic resonance signals in the second scan region, out of a plurality of the first combinations, based on the second volume rate.

20. A method for scanning a predetermined part of a first subject and a second subject to acquire magnetic resonance signals, said method comprising:

calculating a proportion of a scanned area of the predetermined part to an area of a first scan region of the first subject and calculating a position of the predetermined part within the first scan region based on magnetic resonance signals acquired from scanning the first scan region;

predicting a location of the predetermined part from within a second scan region of the second subject based on the proportion and position of the predetermined part calculated for the first subject; and selecting at least one coil element of a plurality of coil elements used to receive each of a plurality of magnetic resonance signals in the second scan region of the second subject based on the predicted location of the predetermined part within the second scan region.

* * * * *